(12) United States Patent
Maier

(10) Patent No.: US 11,654,073 B2
(45) Date of Patent: May 23, 2023

(54) WEARABLE MEDICAL DEVICE FOR PREVENTING AND TREATING CARPAL TUNNEL AND DE QUERVAIN'S SYNDROMES

(71) Applicant: Anodyne Systems LLC, Flowood, MS (US)

(72) Inventor: Joel Elisha Maier, Flowood, MS (US)

(73) Assignee: ANODYNE SYSTEMS LLC, Flowood, MS (US)

( * ) Notice: Subject to any disclaimer, the term of this patent is extended or adjusted under 35 U.S.C. 154(b) by 219 days.

(21) Appl. No.: 17/065,284

(22) Filed: Oct. 7, 2020

(65) Prior Publication Data
US 2022/0104991 A1 Apr. 7, 2022

(51) Int. Cl.
| | | |
|---|---|---|
| A61H 1/02 | (2006.01) | |
| A61F 5/01 | (2006.01) | |
| A61H 1/00 | (2006.01) | |
| A61H 11/00 | (2006.01) | |

(52) U.S. Cl.
CPC .......... *A61H 1/0274* (2013.01); *A61F 5/0118* (2013.01); *A61H 1/006* (2013.01); *A61H 11/00* (2013.01); *A61H 2011/005* (2013.01); *A61H 2201/165* (2013.01); *A61H 2201/1635* (2013.01)

(58) Field of Classification Search
CPC ...... A61H 1/0274; A61H 1/006; A61H 11/00; A61H 2011/005; A61H 1/00; A61H 1/02; A61H 1/0285; A61F 5/0118
See application file for complete search history.

(56) References Cited

U.S. PATENT DOCUMENTS

| | | | |
|---|---|---|---|
| 5,279,545 A * | 1/1994 | Reese, Sr. ............... | A61F 5/013 602/21 |
| 5,702,355 A * | 12/1997 | Repice ................... | A61F 5/0118 602/5 |
| 6,064,912 A | 5/2000 | Kenney | |
| 2003/0199796 A1 | 10/2003 | Yamazaki et al. | |
| 2008/0139986 A1 * | 6/2008 | De Muinck .......... | A61H 1/0274 602/40 |
| 2012/0253244 A1 | 10/2012 | Femano et al. | |
| 2016/0296406 A1 * | 10/2016 | Heyl ......................... | A61F 5/32 |
| 2019/0321249 A1 * | 10/2019 | Maier .................... | A61H 1/006 |

* cited by examiner

*Primary Examiner* — Philip R Wiest
*Assistant Examiner* — Sarah B Lederer
(74) *Attorney, Agent, or Firm* — Knobbe, Martens, Olson & Bear LLP

(57) ABSTRACT

Wearable devices and methods for preventing and treating carpal tunnel syndrome or DeQuervain's syndrome. The wearable device may include a wrist contact portion for receiving a user's forearm, a stretching mechanism configured to apply opposing forces to a first contact portion and a second contact portion to stretch the user's underlying tissue, the first and second contact portions configured to contact the user's forearm, and one or more straps configured to adjust the compressive force being applied to the user's forearm by the first and second contact portions. The first contact portion may be configured to apply a compressive force to the user's forearm at a first location. The second contact portion may be configured to apply a compressive force to the user's forearm at a second location different than the first location.

20 Claims, 22 Drawing Sheets

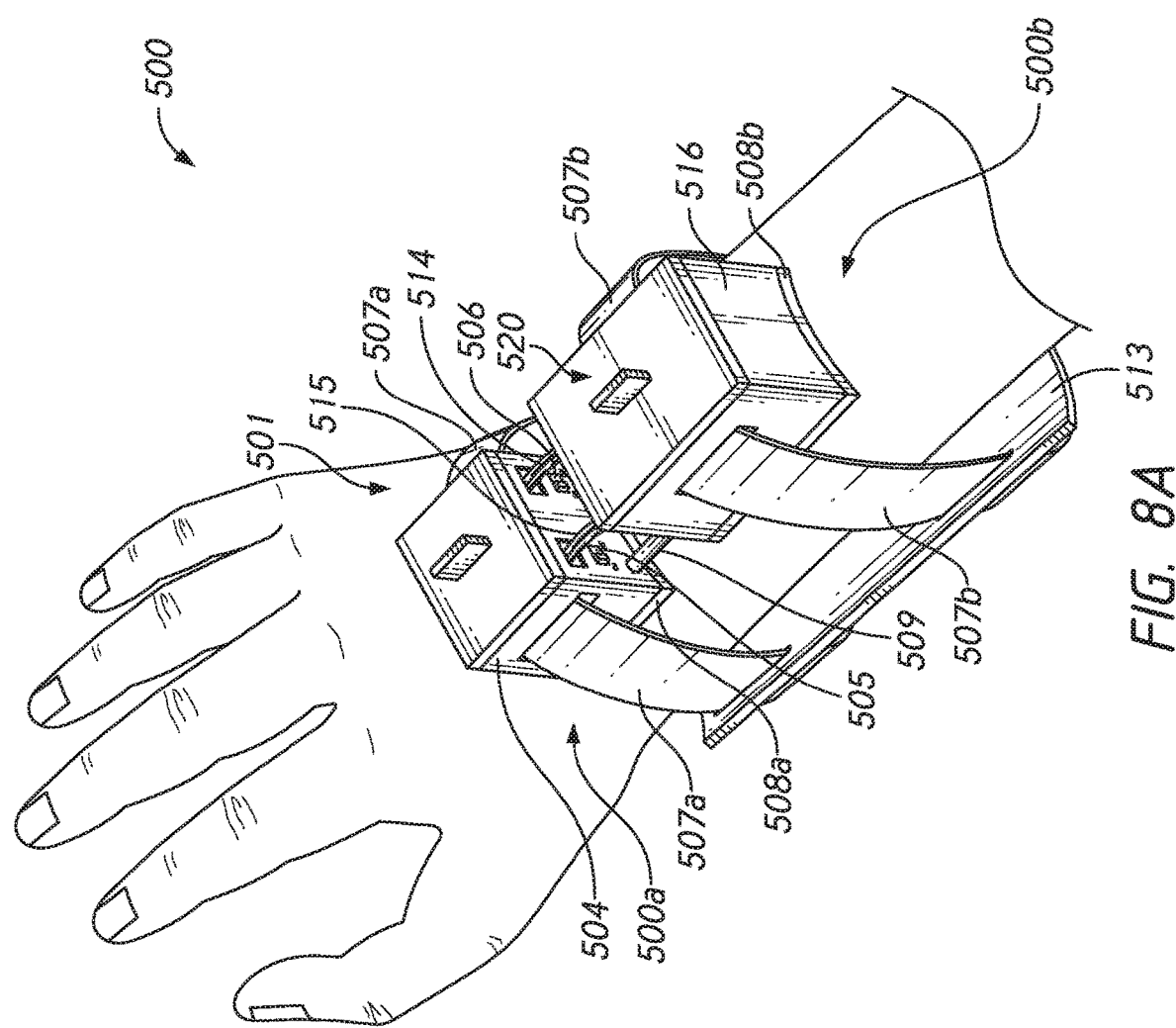

WEARABLE MEDICAL DEVICE FOR PREVENTING AND TREATING CARPAL TUNNEL AND DE QUERVAIN'S SYNDROMES

BACKGROUND

Field

This application relates devices and methods for preventing or treating carpal tunnel and DeQuervain's syndromes.

Description of the Related Art

Many people suffer from carpal tunnel or DeQuervain's syndromes, which causes pain and loss of function in their hands. Carpal tunnel syndrome can be caused by pressure or irritation on the median nerve, which is the nerve that runs from a person's forearm through the carpal tunnel to the person's hand. DeQuervain's syndromes can develop with repetitive motions and overuse of the wrist. Surgical procedures for treating carpal tunnel and DeQuervain's syndromes are expensive, invasive, and, as per all surgeries, risk serious complications. Non-surgical treatments for carpal tunnel or DeQuervain's syndromes usually involve splinting a patient's wrist with a cock-up splint that keeps the patient's wrist in neutral or slight extension. Splints do not work well because they do not directly address the myofascial restrictions present on the back of patient wrists. Non-surgical treatments also take a long time and are not always effective. The lack of effectiveness of non-surgical treatment (and possibly the perceived need to see no other option but for election of surgery) stems from a lack of understanding about the etiology of carpal tunnel and DeQuervain's syndromes, and so do not effectively address the underlying pathology.

SUMMARY

There is a need for a medical device for preventing or treating carpal tunnel and DeQuervain's syndromes by releasing the myofascial restrictions that are the etiological causation for the underlying pathology. Manual release of myofascial restrictions is not always precise, strains the therapist's own hands, and may not produce the required amount of force needed to release said restrictions. The medical devices described herein release the myofascial restrictions by pushing into and spreading the tissues on a posterior side of a person's wrist and forearm, whereby resulting in the release of myofascial restrictions, reducing symptoms of carpal tunnel syndrome. Likewise, the medical devices also release myofascial restrictions along the anatomical distributions of the muscles abductor policis longus and extensor policis brevis to relieve symptoms of DeQuervain's syndrome. These devices remove the human element typically associated with myofascial release.

In some aspects of the disclosure, a wearable device for preventing and/or treating carpal tunnel syndrome or DeQuervain's syndrome is disclosed. The wearable device may be sufficiently small and lightweight to allow the user to freely walk around untethered to tabletop or floor standing equipment. The wearable device may include a support portion for receiving a body part, such as the user's forearm, and a stretching mechanism configured to apply stretching forces to the underlying skin. The stretching mechanism may include one or more contact portions for contacting the body part opposite the support portion. For example, the stretching mechanism may be configured to apply opposing forces to a first contact portion and a second contact portion to stretch the user's underlying tissue. The wearable device may include one or more straps configured to adjust the compressive force being applied to the body part by the first and/or second contact portions. The one or more straps may extend circumferentially around the user's body part in use. The first contact portion can be configured to contact the body part and apply a compressive force to the body part at a first location. The second contact portion can be configured to contact the body part on a same side of the body part as the first contact portion and apply a compressive force to the body part at a second location different than the first location. The first contact portion can be configured to removably connect to the second contact portion, while compressive forces are applied to the user's body part.

The wearable device of the preceding paragraphs or as described further herein can also include one or more of the following features. The stretching mechanism may be configured to apply the opposing forces in a direction generally perpendicular to the compressive forces applied by the first and second contact portions. The one or more straps may be configured to adjust a distance between the first and second contact portions and the support portion. The one or straps may be configured to interface with the support portion. For example, the support portion may include one or more slots. The one or more straps may be configured to pass through the one or more slots. Alternatively, the straps may be integral with or joined to the support portion, for example with adhesive, threading, hook and loop, or otherwise. The one or more straps may include a fastener configured to secure a position of the first and second contact portions relative to the support portion. For example, the fastener could be hook and loop, buttons, hook and eye closure, clips, or otherwise. Alternatively, the one or more straps could be self-adhering without a separate fastener.

The stretching mechanism may include an actuator configured to adjust the stretching forces applied by the stretching mechanism. For example, the first or second contact portion of the stretching mechanism may include an actuator and one or more rods, and the other one of the first or second contact portion of the stretching mechanism may include one or more apertures configured to removably receive the one or more rods. The one or more rods may be configured to transfer a force from the actuator to the one or more apertures such that opposing forces are applied to the first and second contact portions.

In some configurations, the first or second contact portion of the stretching mechanism can be configured to adjust the opposing forces applied by the actuator. For example, the first or second contact portion can include one or more user actuators. The one or more user actuators can be configured to adjust one or more parameters of the opposing forces being applied to the first and second contact portions. The one or more user actuators can be configured to initiate and/or stop the application of the opposing forces to the first and second contact portions. For example, the one or more user actuators can include one or more relay buttons and/or one or more control buttons.

In some configurations, the first or second contact portion of the stretching mechanism may include a screw and the other one of the first or second contact portion of the stretching mechanism may include a threaded hole configured to removably receive the screw. Adjusting the screw may adjust the opposing forces applied to the first and second contact portions. In some configurations, the stretching mechanism may include a spring, for example a compression spring or a torsion spring, to adjust the stretching forces applied by the stretching mechanism. For example, the first or second contact portion of the stretching mechanism may include at least one compression spring positioned over a corresponding compression spring guide and the other one of the first or second contact portion of the stretching mechanism may include at least one spring guide receptor configured to removably receive the corresponding compression spring guide. The at least one compression spring may be configured to apply opposing forces to the first and second contact portions in use. Alternative to a spring, the stretching mechanism may include a mechanical linkage.

The wearable device may include a release mechanism to release the first contact portion from the second contact portion while the first and second contact portions apply compressive forces to the user's body part. The first contact portion may include a first connector and the second contact portion may include a second connector. For example, the first or second connector can include a buckle and the other one of the first or second connector can include a buckle receptor configured to removably receive the buckle. In other configurations, the release mechanism may include clips or hooks.

In some aspects of the disclosure, a method for preventing carpal tunnel syndrome or DeQuervain's syndrome is disclosed. The method may include positioning the user's body part, such as a forearm, on a support portion of a wearable device. When used on the user's forearm, the method can include contacting a first contact portion of the wearable device with a posterior side of the user's forearm over carpal and/or metacarpal bones at a first location and contacting a second contact portion of the wearable device with the posterior side of the user's forearm over a radius and/or an ulna bone at a second location different from the first location. The method can include aligning one or more rods of the first or second contact portion with one or more apertures of the other of the first or second contact portion. The method can also include applying a compressive force to the user's body part, for example using one or more straps connected to the first and second contact portions and the support portion. The method can also include applying opposing forces to the first contact portion and the second contact portion using a stretching mechanism to stretch the user's tissue.

The method of the preceding paragraph or as described further herein can also include one or more of the following features. Applying the opposing forces may include applying the opposing forces in a direction generally perpendicular to the compressive force applied by the first and second contact portions.

The method of the preceding paragraph or as described further herein can also include one or more of the following features. The stretching mechanism can include an actuator configured to apply a force to the one or more rods of the first or second contact portion. The one or more rods can transfer the force from the actuator to the one or more apertures such that the opposing forces are applied to the first and second contact portions.

The method can include, prior to applying opposing forces to the first and second contact portions, setting one or more user parameters to apply opposing forces to the first and second contact portions according to the one or more user parameters. The one or more user parameters can comprise a forward period of time, one or more stop periods of time, and/or a reverse period of time. The one or more stop periods of time can comprise a first stop period of time with the actuator engaged and in a forward position. The one or more stop periods of time can comprise a second stop period of time with the actuator disengaged and in a reverse position. The one or more stop period of time can include the same period of time or different periods of time. Applying the opposing forces to the first and second contact portions can include: automatically initiating the application of the opposing forces for the forward period of time; automatically applying the opposing forces to the first and second contact portions for the first stop period of time; automatically releasing the opposing forces applied to the first and second contact portions for the reverse period of time; and automatically allowing the user's tissue to rest for the second stop period of time. The method can include, after automatically allowing the user's tissue to rest: automatically reinitiating the application of the opposing forces for the forward period of time; automatically reapplying the opposing forces for the first stop period of time; automatically releasing the opposing forces for the reverse period of time; and automatically allowing the user's tissue to rest for the second stop period of time until treatment is complete.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 8A is a perspective view of a wearable medical device being worn by a user.

DETAILED DESCRIPTION

The present application relates to wearable medical devices for preventing or treating carpal tunnel and DeQuervain's syndromes. The wearable devices described herein are adapted to receive and support a user's forearm and release myofascial restrictions by selectively pushing into and spreading the relevant wrist and forearm tissue with adjustable vertical (generally anterior-posterior direction) and non-vertical forces. The forearm can include any portion of the user's forearm from the elbow to the fingertips. These wearable devices can be used under the supervision of a physical therapist, an occupational therapist, or a doctor or in the patient's home.

FIGS. 1-3C illustrate a wearable medical device 100 and different components of the wearable medical device 100 for preventing or treating carpal tunnel and DeQuervain's syndromes, which may include any feature of the other embodiments described herein. The wearable device 100 is designed to allow a user to walk or move around, while the device is in use.

Figure 1:
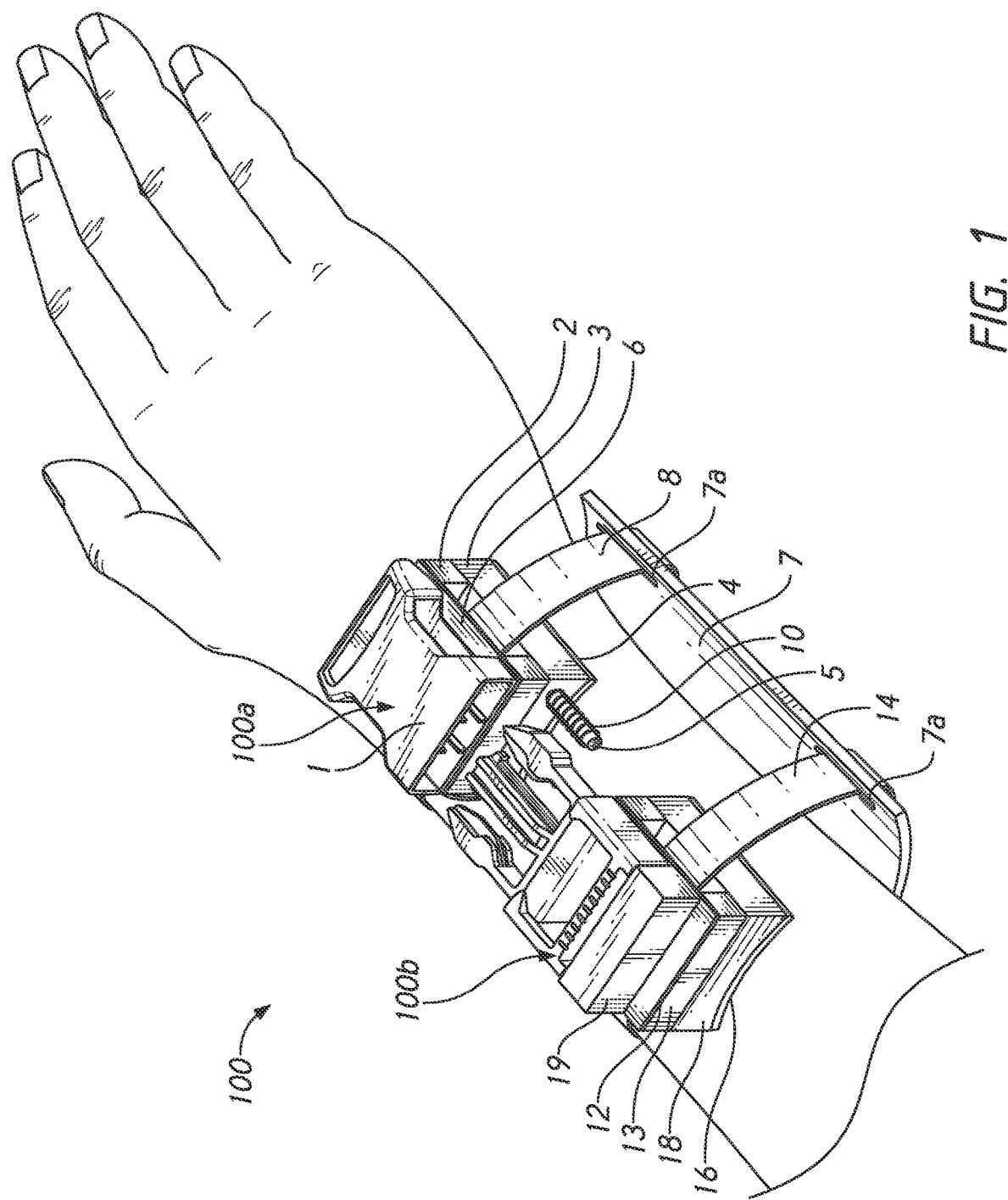
FIG. 1 is a perspective view of a wearable medical device being worn by a user.

As shown in FIG. 1, the wearable device 100 can generally include a release mechanism, a stretching mechanism, one or more straps 8, 14, a wrist contact portion 7 for receiving a user's forearm, and/or one or more contact portions 100a, 100b for contacting the user's arm opposite the wrist contact portion 7. The release mechanism enables the user to releasably connect the one or more contact portions 100a, 100b such that the user is able to engage the stretching mechanism and adjust the one or more straps 8, 14 of the wearable device 100. The one or more contact portions 100a, 100b can include a first contact portion 100a to contact the user's forearm at a first location and a second contact portion 100b to contact the user's forearm at a second location, different from the first location. Once the stretching mechanism is engaged and the one or more straps 8, 14 are adjusted, the release mechanism can be released such that the stretching mechanism can apply force to the first and second contact portion 100a, 100b in opposing directions.

The release mechanism can include a first connector 1 of the first contact portion 100a and a second connector 11 of the second contact portion 100b. The second connector 11 can be adapted to removably receive the first connector 1 or vice versa. For example, the release mechanism can include a buckle, such as a side release buckle. The first connector 1 can be a buckle frame or receptor 1 and the second connector 11 can be a buckle prong 11 with a buckle bolster 19. Alternatively, the first connector 1 can comprise the buckle prong and the second connector 11 can comprise the buckle frame or receptor. Other connectors or attachment mechanisms, such as a latch, a screw, or the like, can be used.

Figure 2A:
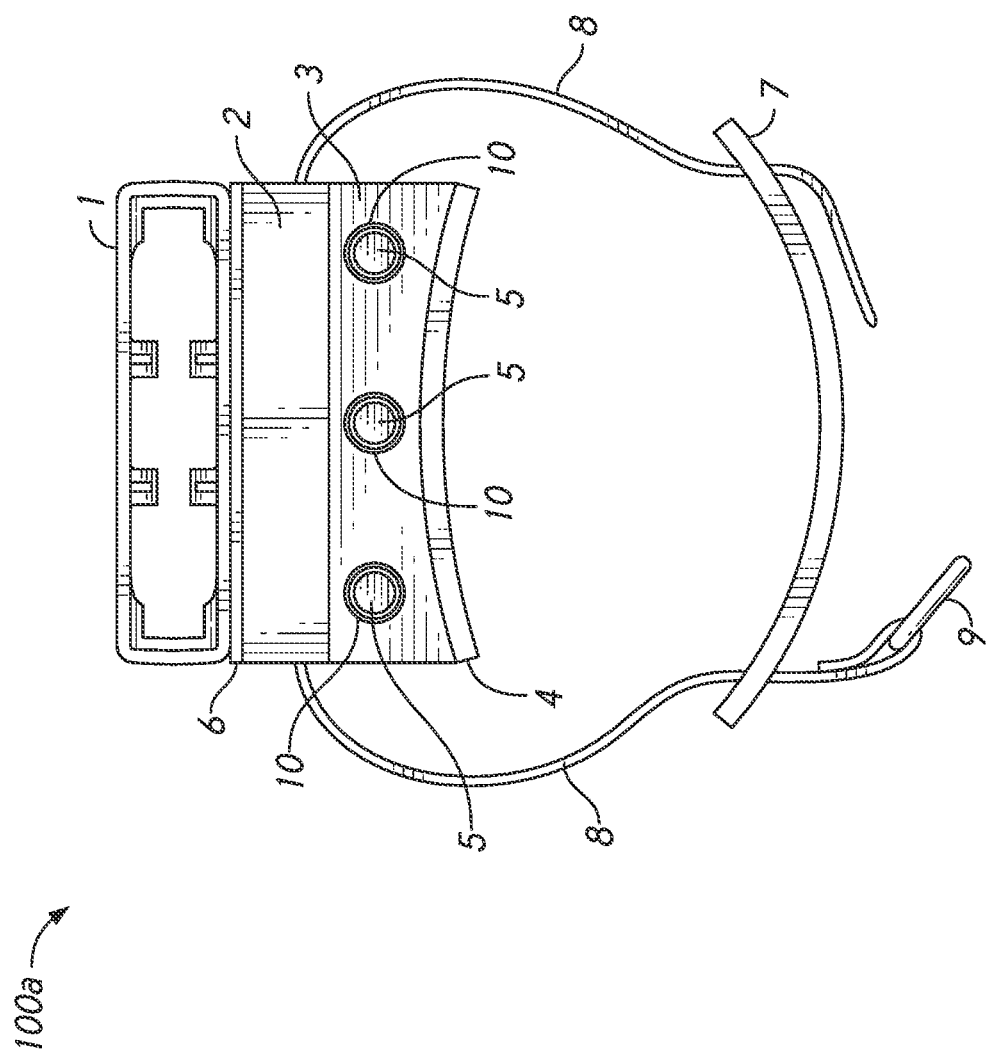
FIG. 2A is a front view of a first contact portion of a wearable medical device.
Figure 2B:
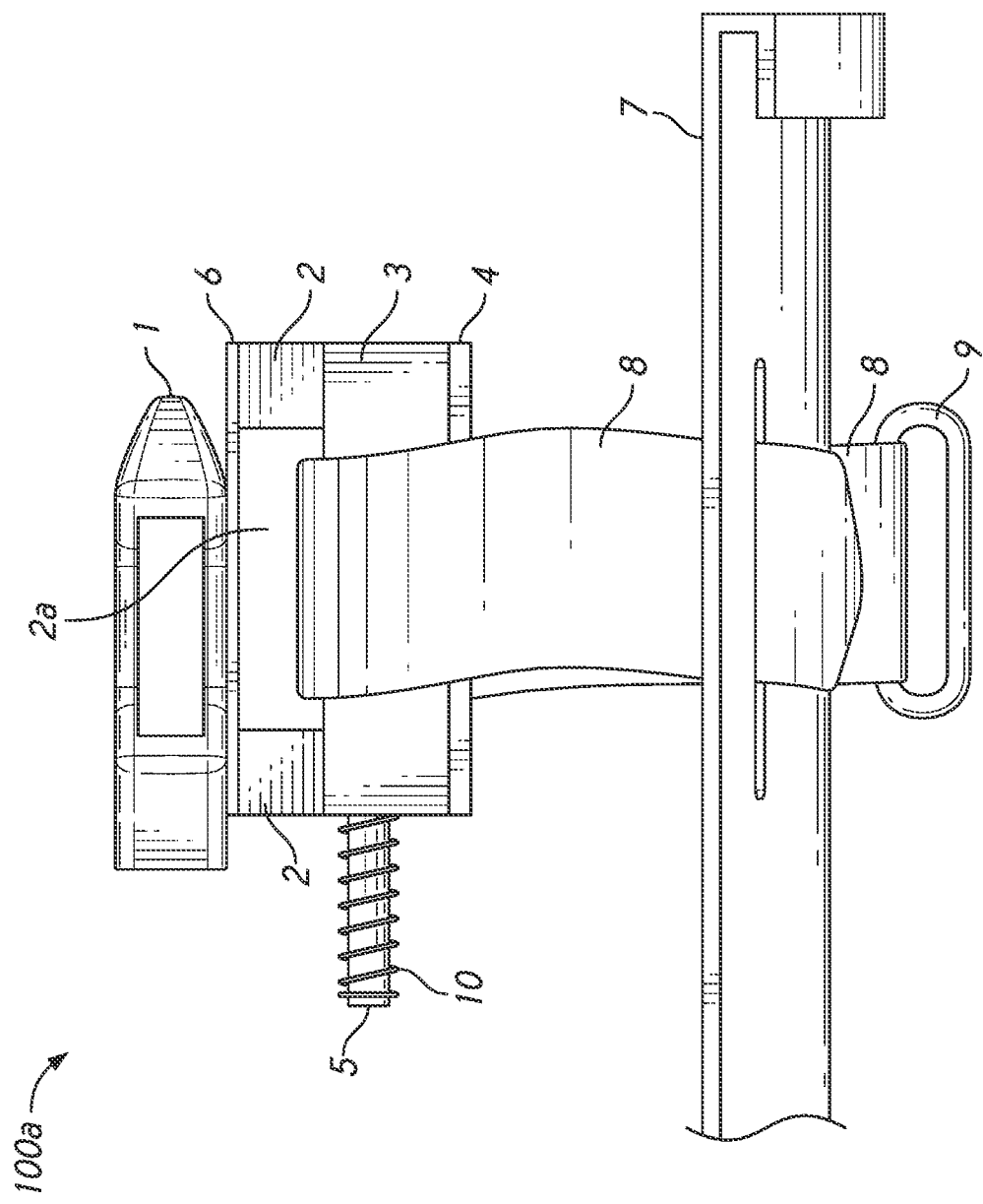
FIG. 2B is a side view of the first contact portion of the wearable medical device shown in FIG. 2A.
Figure 2C:
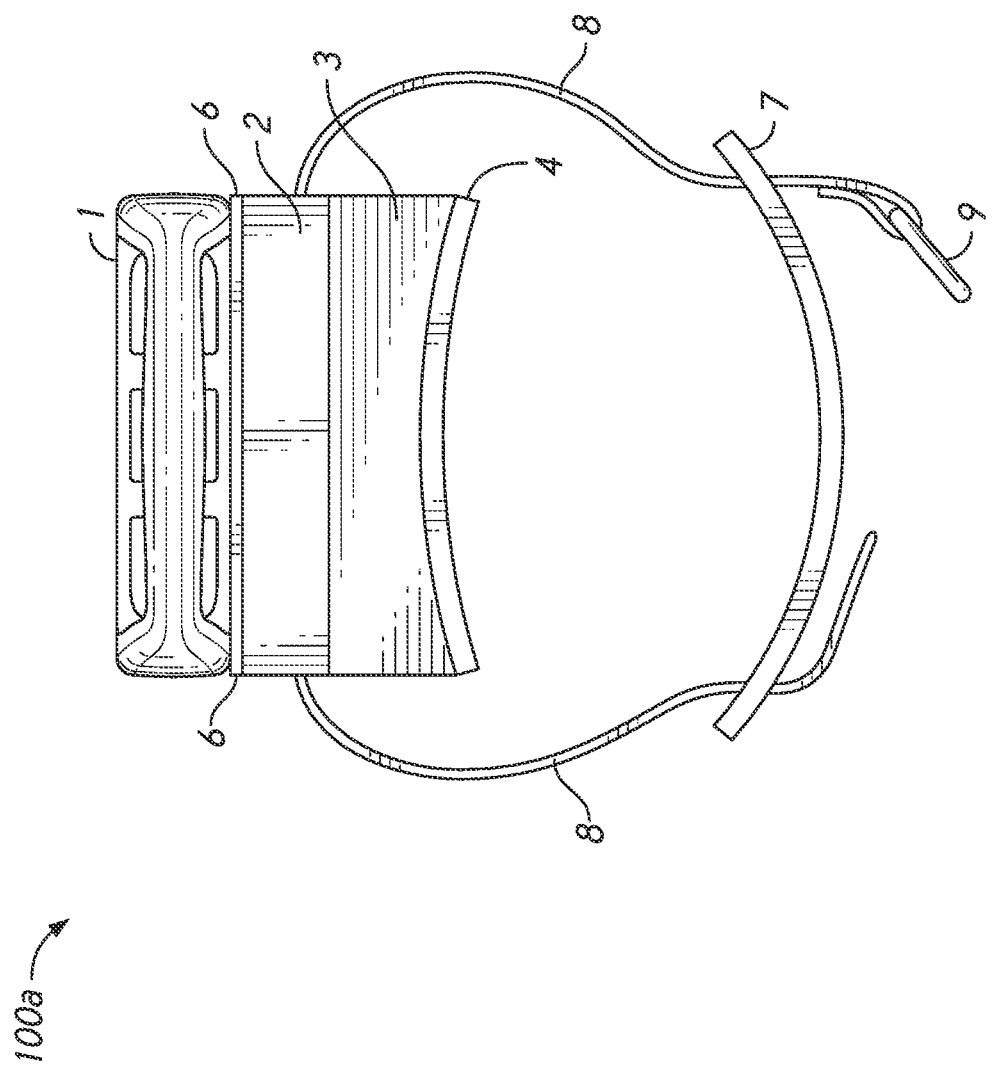
FIG. 2C is a back view of the first contact portion of the wearable medical device shown in FIG. 2A.

As previously described, the wearable device 100 can include a stretching mechanism configured to apply opposing forces to the first and second contact portions 100a, 100b to stretch the user's tissue. The stretching mechanism may include one or more springs 10 configured to apply opposing forces to the first and second contact portions 100a, 100b. The stretching mechanism may include a spring holder 3 of the first contact portion 100a and a spring accepter 18 of the second contact portion 100b. The spring holder 3 may support the one or more springs 10 disposed over one or more spring guides 5, as shown in FIGS. 1-2B. The one or more spring guides 5 can extend from the spring holder 3, as shown in FIG. 2B. The spring accepter 18 may include one or more spring guide holes 15 that can be adapted to removably receive the one or more spring guides 5 such that the one or more spring 10 are compressed between the first contact portion 100a and the second contact portion 100b. The one or more compressed springs 10 can apply opposing forces to the first and second contact portions 100a, 100b.

As shown in FIGS. 1-3C, the wearable device 100 can include the wrist contact portion 7 for receiving a user's forearm. The wrist contact portion 7 may be constructed of a flexible material that enables the wrist contact portion 7 to be bent around the user's arm. For example, the wrist contact portion 7 may include a flexible fabric, elastic, plastic, rubber, or other material. The wrist contact portion 7 may define an arcuate shape and be adapted to support the forearm of the user. However, the wrist contact portion 7 may take on any configuration suitable for the patient to rest their forearm during treatment. For example, the wrist contact portion 7 may provide a planar surface for the user to rest their forearm. The wrist contact portion 7 may include one or more slots 7a that can be configured to receive a portion of the one or more straps 8, 14, which is further described below. The one or more slots 7a can be arranged near a periphery of the wrist contact portion 7.

The first and second contact portions 100a, 100b of the wearable device 100 can be adapted to transfer the vertical and/or non-vertical forces to the underlying tissue. For example, the first and second contact portions 100a, 100b may apply a compressive force to the user's forearm in a posterior-anterior direction. The two contact portions 100a, 100b may be adjusted relative to each other such that the contact portions 100a, 100b can be properly positioned. For example, a first contact portion 100a may be positioned over the user's carpal and/or metacarpal bones and a second contact portion 100b may be positioned over the user's radius and/or ulna bones. Each contact portion 100a, 100b may include a contact interface 4, 16 and a strap of the one or more straps 8, 14. The contact interfaces 4, 16 can be adapted for patient comfort when engaging the first and second contact portions 100a, 100b and/or to adhere or secure the respective contact portion 100a, 100b to the user's skin. For example, the contact interfaces 4, 16 can include padding. The one or more straps 8, 14 may be adapted to adjust the compressive force applied to the user's forearm by the first and second contact portions 100a, 100b. For example, a user can adjust the compressive force applied by the one or more contact portions 100a, 100b by tightening or loosening the one or more straps 8, 14. Each contact portion 100a, 100b can optionally include a spacer 2, 13 with a spacer top 6, 12. The spacers 2, 13 can be positioned between the connectors 1, 11 and the contact interfaces 4, 16 of the first and second contact portions 100a, 100b.

Figure 3A:
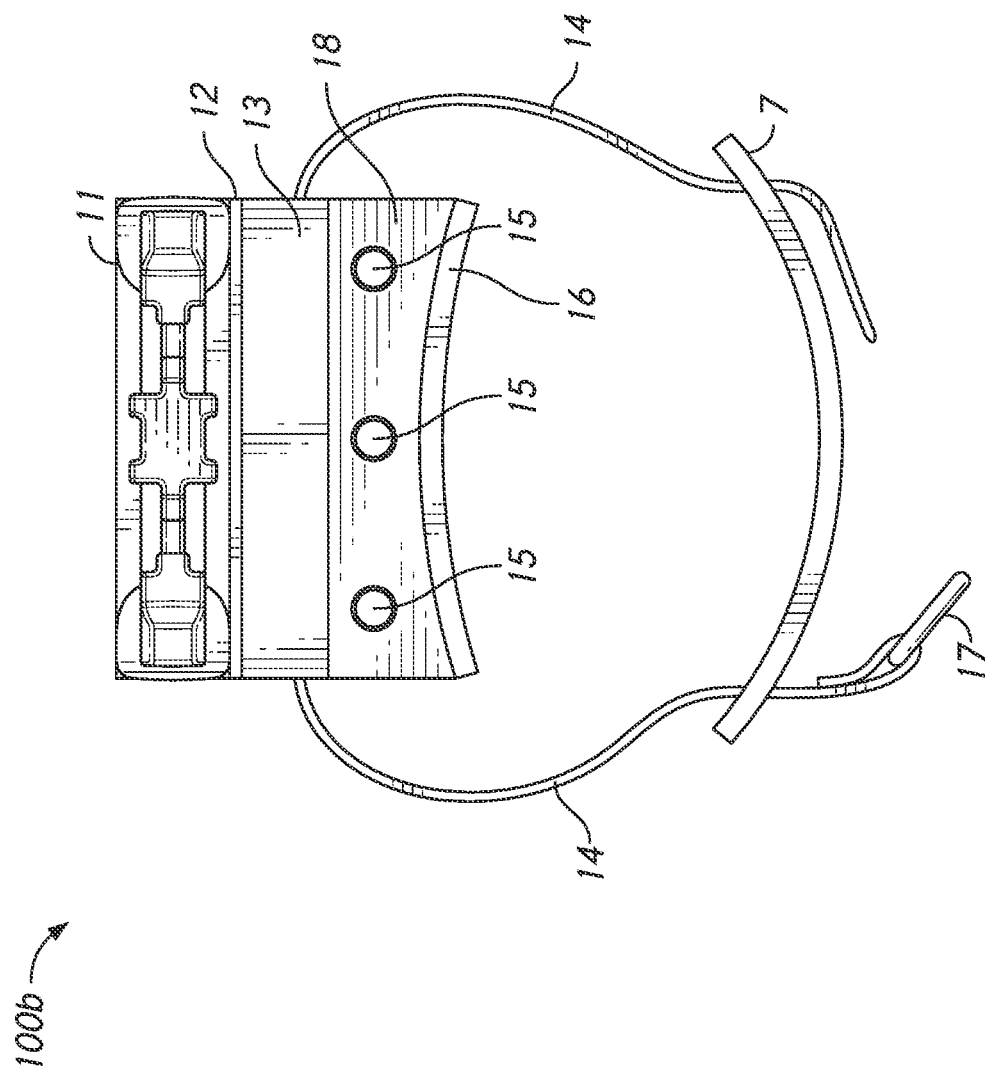
FIG. 3A is a front view of a second contact portion of a wearable medical device.
Figure 3B:
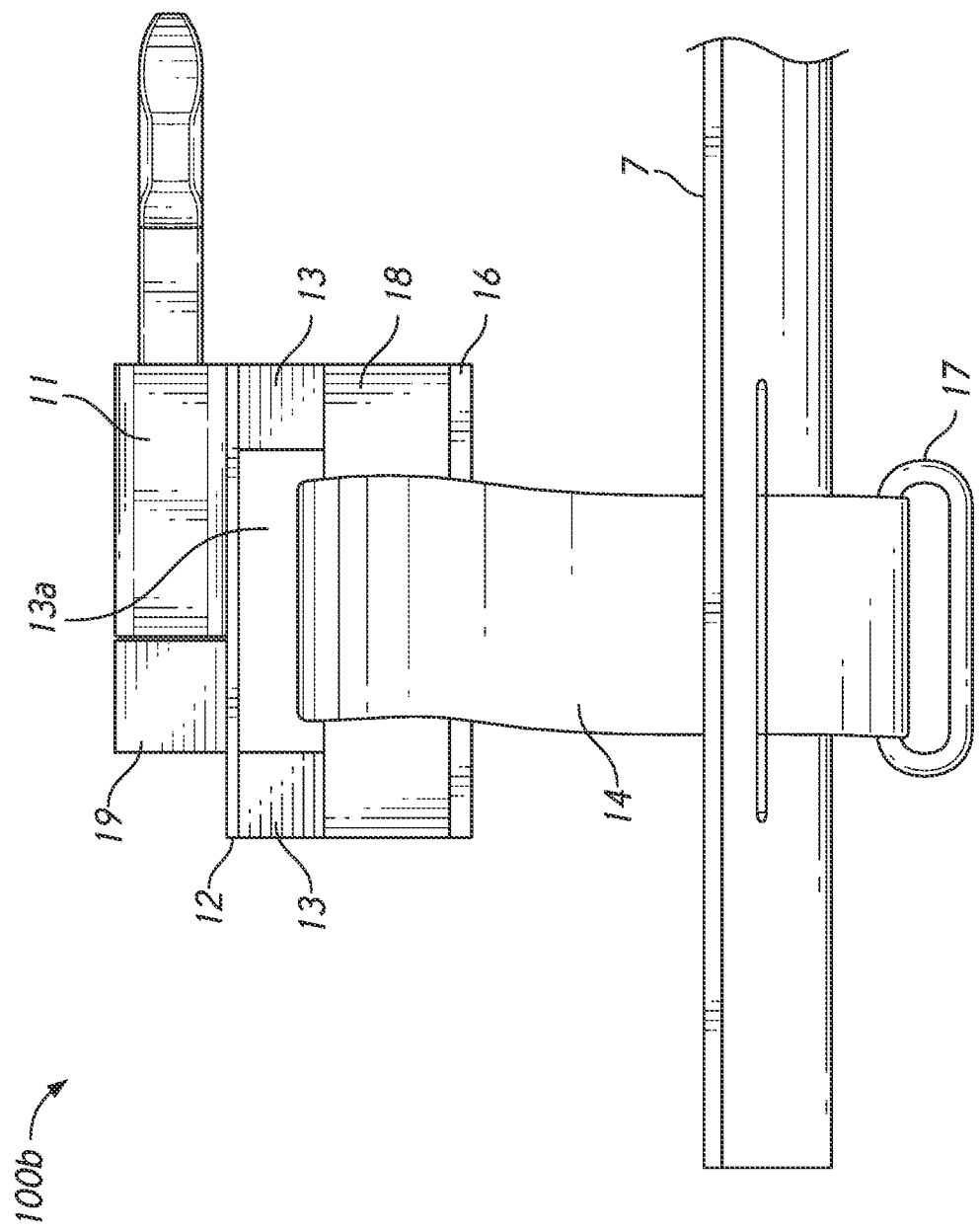
FIG. 3B is a side view of the second contact portion of the wearable medical device shown in FIG. 3A.
Figure 3C:
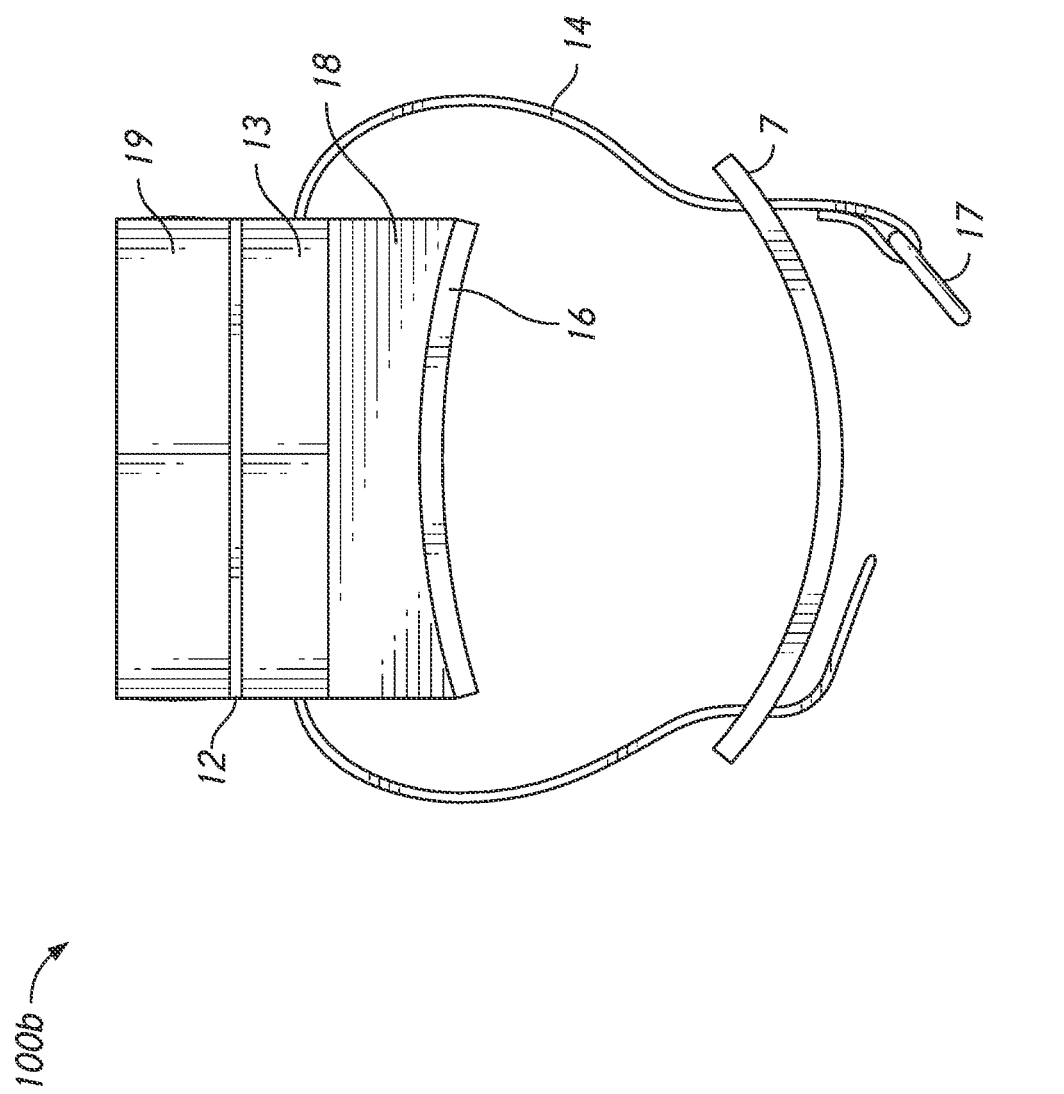
FIG. 3C is a back view of the second contact portion of the wearable medical device shown in FIG. 3A.

As shown in FIGS. 2B and 3B, the contact portions 100a, 100b can include a through-hole 2a, 13a that extends from one side of the spacer 2, 13 to the other side of the spacer 2, 13. The length of the through-hole 2a, 13a can be substantially perpendicular to a longitudinal axis of the wearable device 100. Each of the through-holes 2a, 13a can be adapted to receive at least one of the one or more straps 8, 14. For example, the through-hole 2a can receive a first strap 8 and the through-hole 13a can receive a second strap 14. The first strap 8 can be adapted to change a distance between the first contact portion 100a and the wrist contact portion 7, and the second strap 13 can be adapted to change a distance between the second contact portion 100b and the wrist contact portion 7. Although the straps 8, 14 are illustrated as extending through the spacers 2, 13, in other configurations, the straps 8, 14 may extend over the contact portions 100a, 100b.

The first and second straps 8, 14 can include a strap tightener 9, 17 and a fastener adapted to secure a position of the respective contact portion 100a, 100b relative to the wrist contact portion 7. For example, the fastener can include a hook and loop fastener, such as Velcro®. In other configurations, the straps 8, 14 may be self-adhering without a separate fastener. Each strap tightener 9, 17 can be adapted to assist the user in adjusting the first and second straps 8, 14 to change the compressive force applied by the respective contact portion 100a, 100b. For example, one or both of the strap tighteners 9, 17 may include a loop 9, 17 that may be constructed of a material sufficient to withstand the forces applied by the user. The loop(s) 9, 17 can be constructed of a plastic material, a metal material, a combination of materials, or the like.

In use, as shown in FIG. 1, a user can place their forearm between the wrist contact portion 7 and the first and second contact portions 100a, 100b. The user can position one of the contact portions 100a, 100b on top of the user's carpal and/or metacarpal bones and the other contact portion 100a, 100b over the user's radius and/or ulna bones. The user can insert the spring guides 5 into the spring guide holes 15, and connect the first and second connectors 1, 11 to engage the release mechanism. The user can adjust the one or more straps 8, 14 until the desired compressive forces are applied. After the user secures the one or more straps 8, 14, the user can release the release mechanism by disconnecting the first and second connectors 1, 11 such that the one or more compressed springs 10 applies opposing forces against the first and second contact portions 100a, 100b. The user can utilize the device 100 to intermittently or statically stretch the tissue on the user's wrist. Intermittent stretching can make the stretching procedure more comfortable for the user since it allows the user's tissue to rest between stretches. For static stretching, the user can set up the medical device 100 and allow it to stretch the user's forearm for a period of time (e.g., less than or equal to about 30 minutes, less than or equal to about 1 hour). For intermittent stretching, the user can, for example, allow the medical device 100 to apply forces to the user's forearm for a set period of time, for example at least about 5 seconds and/or less than or equal to about 1 minute (e.g., 5 seconds, 10 seconds, 15 seconds, 30 seconds). After the set period of time, the user can release the forces for a set period of time, for example at least about 5 seconds and/or less than or equal to about 1 minute (e.g., 5 seconds, 10 seconds, 15 seconds, 30 seconds). The user can continue to reapply the forces and release the forces until the procedure is completed (e.g., less than or equal to about 30 minutes, less than or equal to about 1 hour).

Figure 4A:
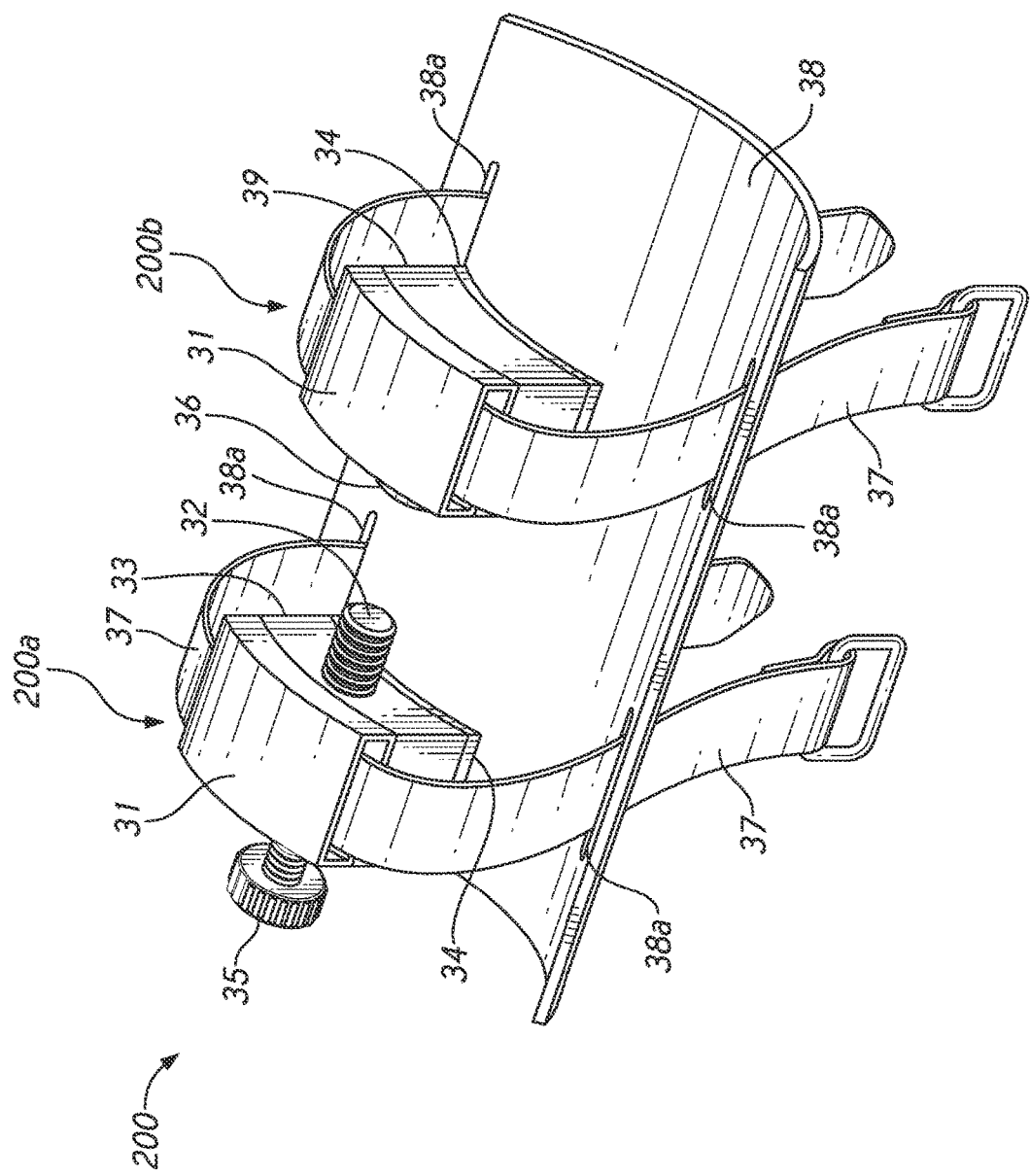
FIGS. 4A-4B are perspective views of a wearable medical device.
Figure 4B:
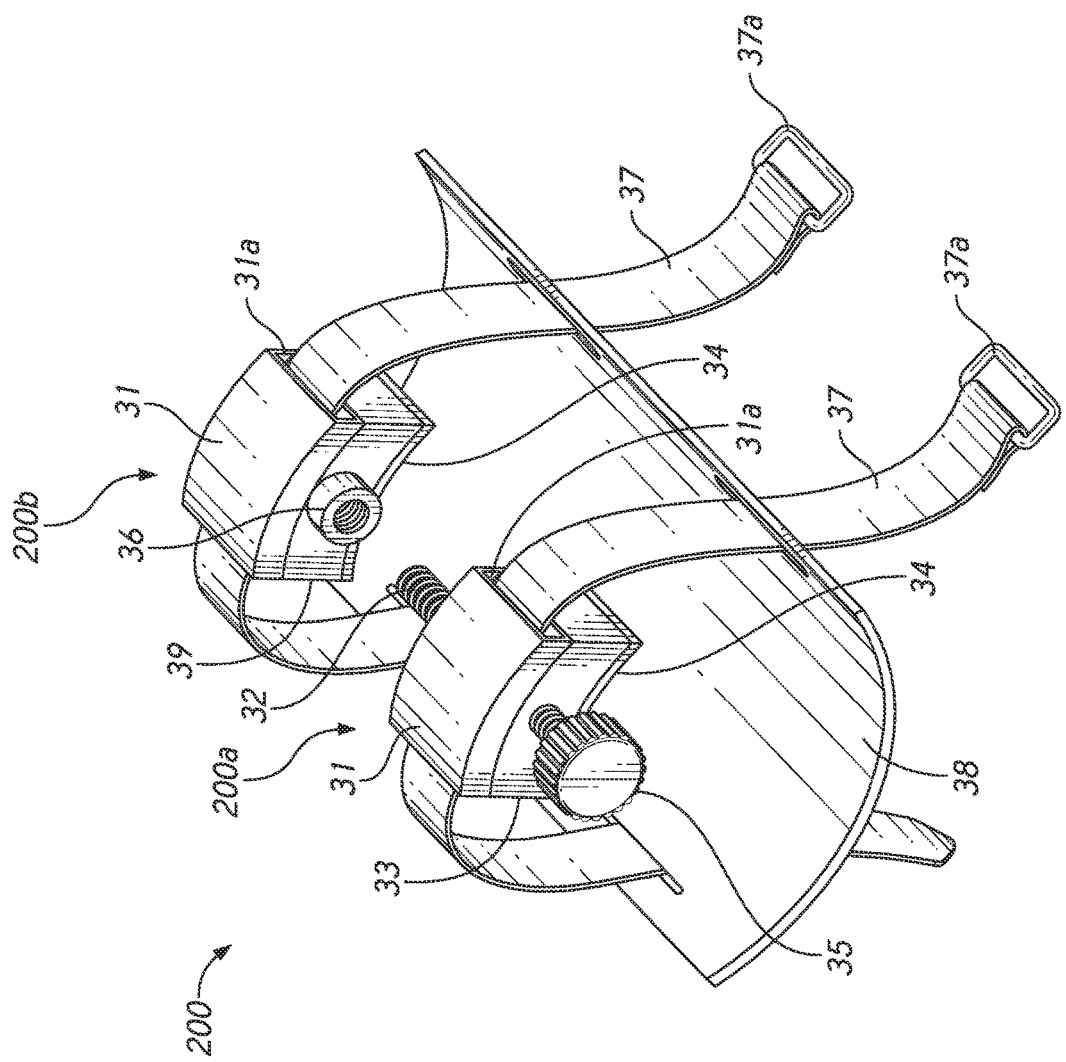
Figure 4C:
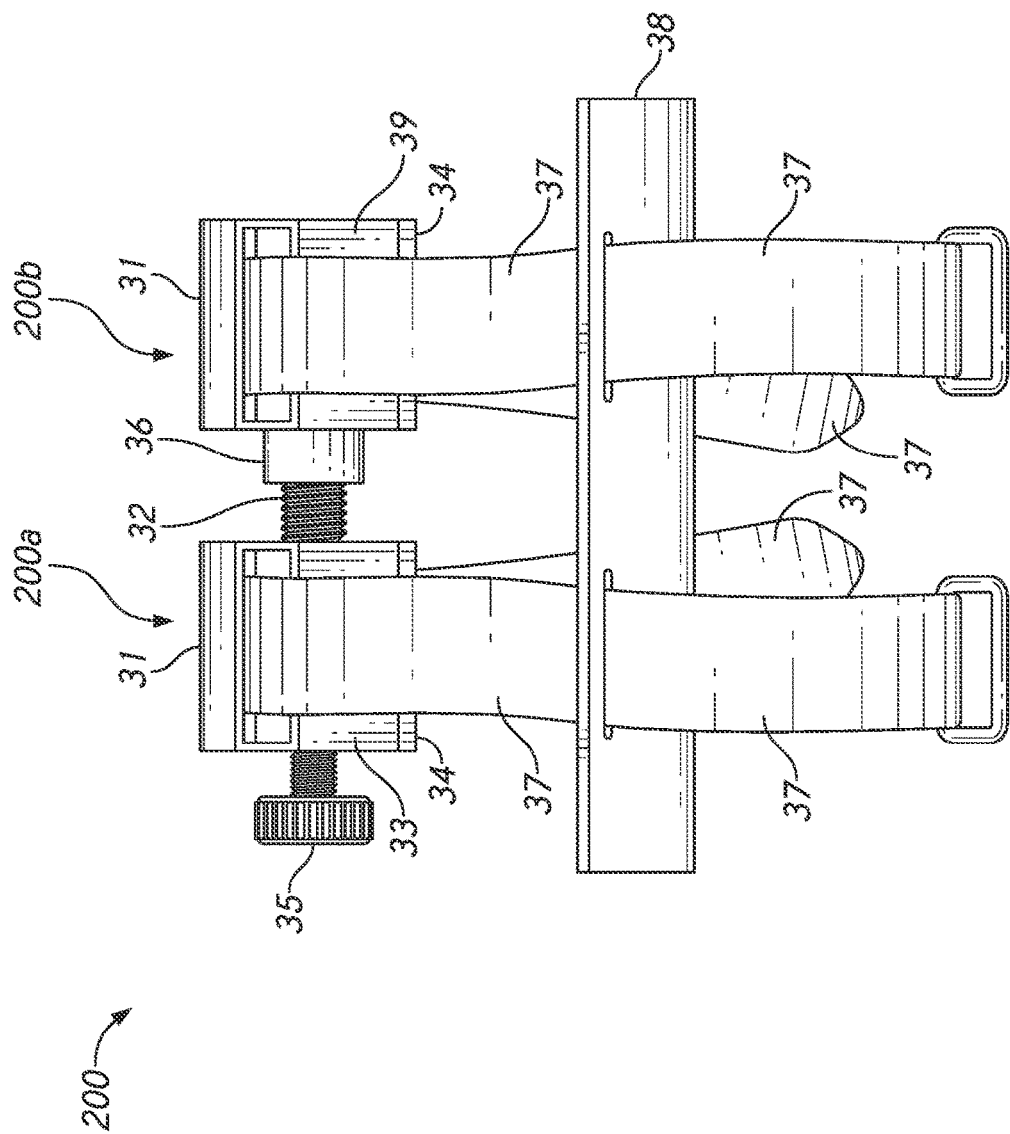
FIG. 4C is a side view of the wearable medical device shown in FIGS. 4A-4B.

With reference to FIGS. 4A-4C, another configuration of a wearable medical device 200 is shown. The wearable device 200 resembles or is identical to the medical device 100 discussed above in many respects. Any component or step disclosed in any embodiment in this specification can be used in any other embodiment.

As shown in FIGS. 4A-4C, the wearable device 200 can generally include a stretching mechanism, one or more straps 37, a wrist contact portion 38 for receiving a user's forearm, and/or one or more contact portions 200a, 200b for contacting the user's arm opposite the wrist contact portion 37. The stretching mechanism can be configured to apply opposing forces to the one or more contact portions 200a, 200b to stretch the user's tissue. The one or more contact portions 200a, 200b can include a first contact portion 200a to contact the user's forearm at a first location and a second contact portion 200b to contact the user's forearm at a second location, different from the first location. The stretching mechanism may include a first connector body 33 of the first contact portion 200a and a second connector body 39 of the second contact portion 200b. The first connector body 33 can include a first connector 35 and the second connector body 39 can include a second connector 36 configured to engage with the first connector 35. For example, the first connector body 33 can be a screw holder body 33 that supports a screw 35 with a distal end 32 and the second connector body 39 can be a screw receptor body 39 that includes a screw receptor 36, such as a threaded hole, configured to removably receive the distal end 32 of the screw 35. Alternatively, the first connector 35 can be the screw receptor and the second connector 36 can include the screw. To engage the stretching mechanism, the user can position the screw 35 in the screw receptor 36 and tighten the screw 35 until the screw receptor 36 engages the screw holder 39 of the first contact portion 200a such that the screw receptor 36 pushes the contact portions 200a, 200b in opposing directions.

The wearable device 200 can include a wrist contact portion 38 for receiving a user's forearm. The wrist contact portion 38 may be constructed of a flexible material that enables the wrist contact portion 38 to be bent around the user's arm. For example, the wrist contact portion 38 may include a flexible fabric, elastic, plastic, rubber, or other material. The wrist contact portion 38 may define an arcuate shape and be adapted to support the forearm of the user. However, the wrist contact portion 38 may take on any configuration suitable for the patient to rest their forearm during treatment. For example, the wrist contact portion 38 may provide a planar surface for the user to rest their forearm. The wrist contact portion 38 may include one or more slots 38a that can be configured to receive a portion of the one or more straps 37, which is further described below. The one or more slots 38a can be arranged near a periphery of the wrist contact portion 38.

The first and second contact portions 200a, 200b of the wearable device 200 can be adapted to transfer the vertical and/or non-vertical forces to the underlying tissue. For example, the first and second contact portions 200a, 200b may apply a compressive force to the user's forearm in a posterior-anterior direction. The two contact portions 200a, 200b may be adjusted relative to each other such that the contact portions 200a, 200b can be properly positioned. For example, a first contact portion 200a may be positioned over the user's carpal and/or metacarpal bones and a second contact portion 200b may be positioned over the user's radius and/or ulna bones. Each contact portion 200a, 200b may include a contact interface 34 and a strap of the one or more straps 37. The contact interfaces 34 can be adapted for patient comfort when engaging the first and second contact portions 200a, 200b and/or to adhere or secure the respective contact portion 200a, 200b to the user's skin. For example, the contact interfaces 34 can include padding. The one or more straps 37 may be adapted to adjust the compressive force applied to the user's forearm by the first and second contact portions 200a, 200b. For example, a user can adjust the compressive force applied by the one or more contact portions 200a, 200b by tightening or loosening the one or more straps 37.

As shown in FIGS. 4A-4C, each contact portion 200a, 200b can include a strap holder 31 adapted to receive a strap of the one or more straps 37. For example, the strap holder 31 can include a through-hole 31a that can extend substantially perpendicular to a longitudinal axis of the wearable device 200. Each of the through-holes 31a can be adapted to receive at least one of the one or more straps 37. For example, the through-hole 31a of the first contact portion 200a can receive a first strap 37 and the through-hole 31a of the second contact portion 200b can receive a second strap 37. The first strap 37 of the first contact portion 200a can be adapted to change a distance between the first contact portion 200a and the wrist contact portion 38, and the second strap 37 of the second portion 200b can be adapted to change a distance between the second contact portion 200b and the wrist contact portion 38.

The straps 37 can include a strap tightener 37a and a fastener adapted to secure a position of the respective contact portion 200a, 200b relative to the wrist contact portion 38. For example, the fastener can include a hook and loop fastener, such as Velcro®. The strap 37a can be adapted to assist the user in changing the compressive force applied by the contact portion 200a, 200b. In other configurations, the straps 37 may be self-adhering without a separate fastener. Each strap tightener 37 can be adapted to assist the user in adjusting the straps 37 to change the compressive force applied by the respective contact portion 200a, 200b. For example, one or both of the strap tighteners 37 may include a loop 37 that may be constructed of a material sufficient to withstand the forces applied by the user. The loop(s) 37 can be constructed of a plastic material, a metal material, a combination of materials, or the like.

In use, a user can place their forearm between the wrist contact portion 38, and the first and second contact portions 200a, 200b. The user can position one of the contact portions 200a, 200b on top of the user's carpal and/or metacarpal bones and the other contact portion 200a, 200b over the user's radius and/or ulna bones. The user can insert the screw 35 into the screw receptor 36 and tighten the one or more straps 37 until the desired compressive force is applied. After the user secures the one or more straps 37, the user can tighten the screw 35 until the screw holder body 33 of the first contact portion 200a pushes against the screw receptor 36 of the second contact portion 200b such that the two contact portions 200a, 200b are pushed in opposing directions. The user can utilize the device 200 to intermittently or statically stretch the tissue on the user's wrist. For static stretching, the user can set up the medical device 200 and allow it to stretch the user's forearm for a period of time (e.g., less than or equal to 5 minutes, less than or equal to 15 minutes, less than or equal to 30 minutes, less than or equal to 1 hour). For intermittent stretching, the user can, for example, allow the medical device 200 to apply forces to the user's forearm for a set period of time, for example at least about 10 seconds and/or less than or equal to about 1 minute (e.g., 10 seconds, 15 seconds, 30 seconds). After the set period of time, the user can release the forces for a set period of time, for example at least about 10 seconds and/or less than or equal to about 1 minute (e.g., 10 seconds, 15 seconds, 30 seconds). The user can continue to reapply the forces and release the forces until the procedure is completed (e.g., less than or equal to 5 minutes, less than or equal to 15 minutes, less than or equal to 30 minutes, less than or equal to 1 hour).

With reference to FIGS. 5A-5E, another configuration of a wearable medical device 300 is shown. The wearable device 300 resembles or is identical to the medical device 100 discussed above in many respects. Any component or step disclosed in any embodiment in this specification can be used in any other embodiment.

Figure 5A:
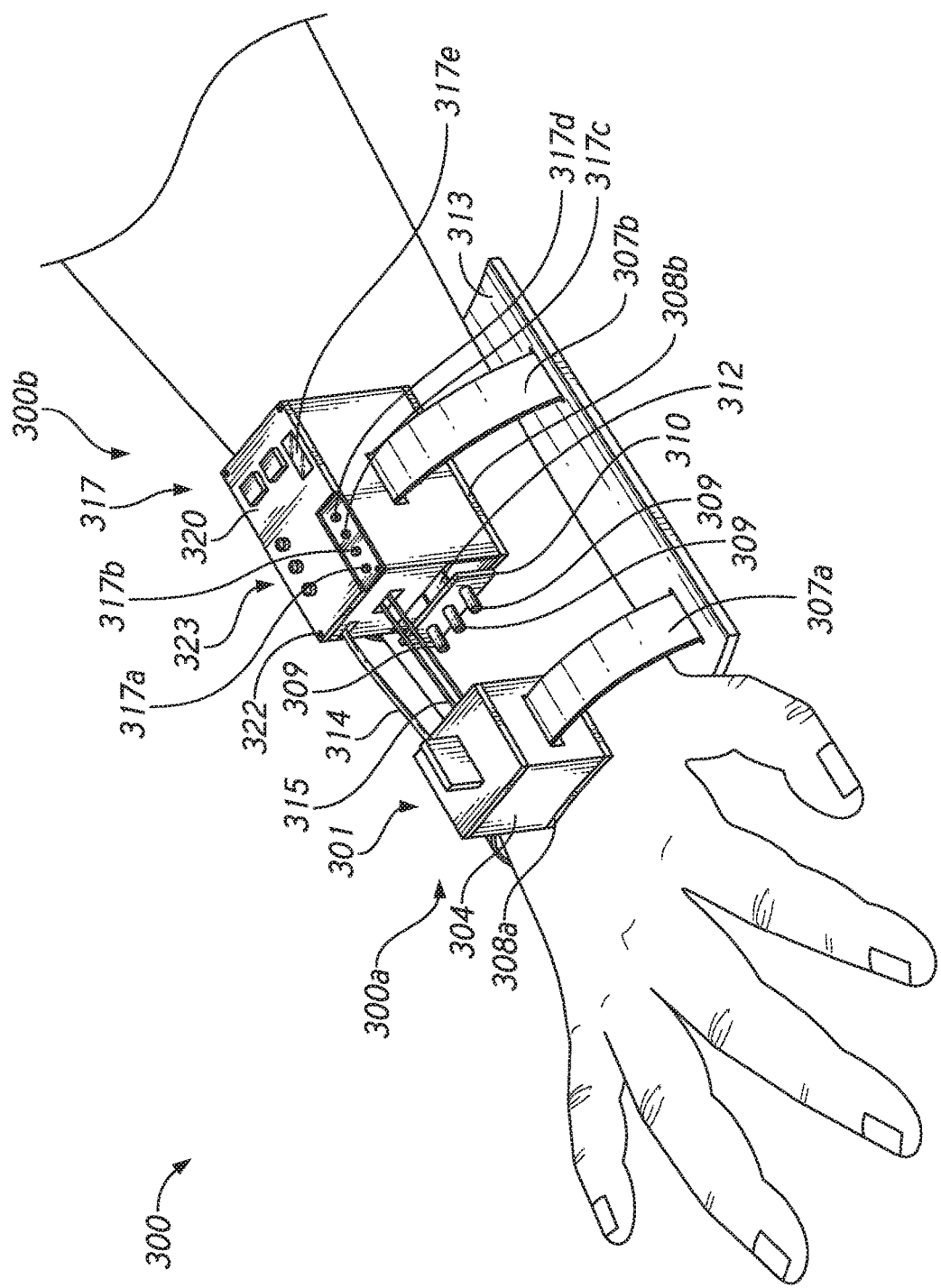
FIG. 5A is a perspective view of a wearable medical device being worn by a user.
Figure 5B:
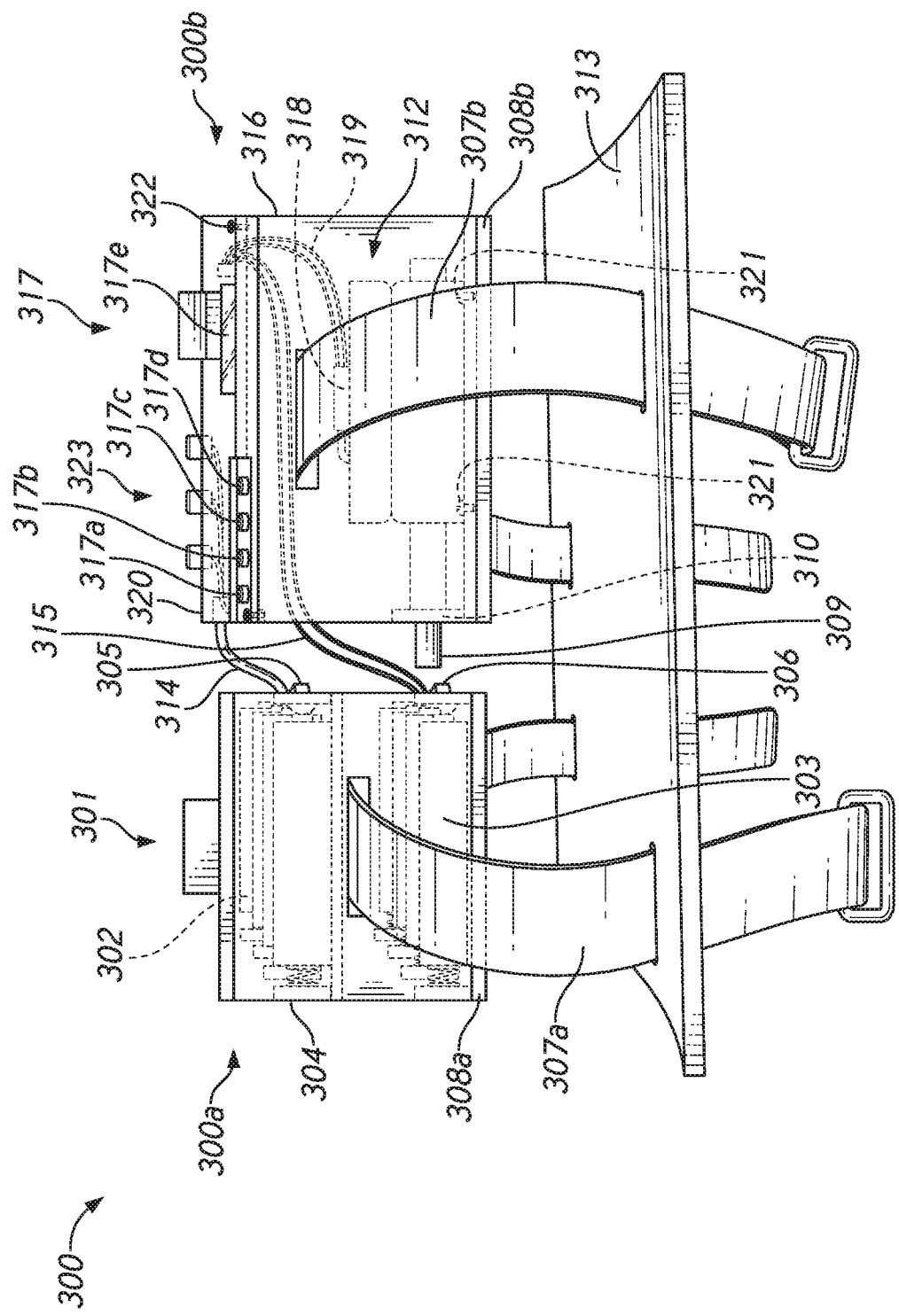
FIG. 5B is a partial cross-sectional side view of the wearable medical device shown in FIG. 5A.
Figure 5C:
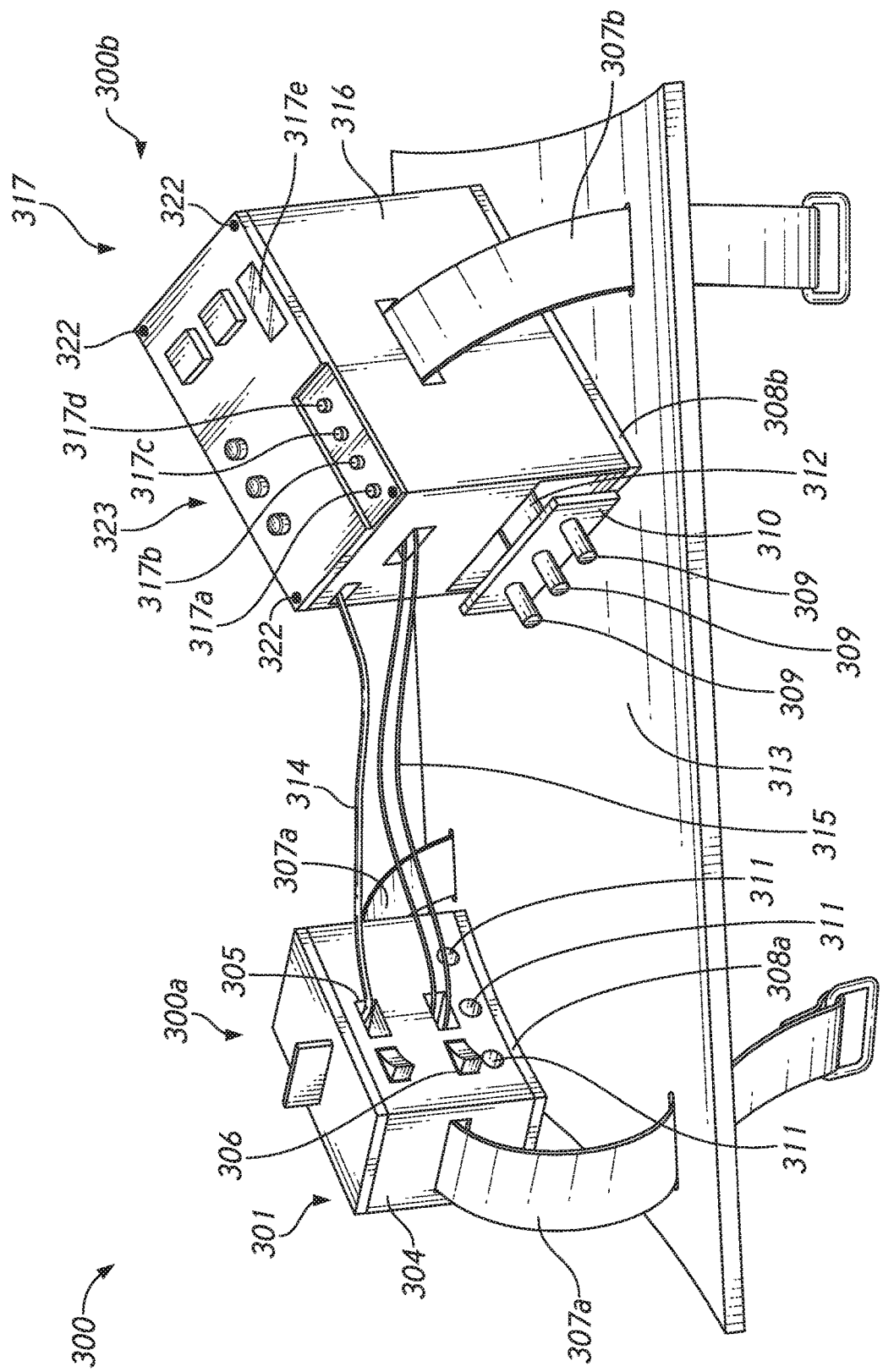
FIG. 5C is a perspective view of the wearable medical device shown in FIG. 5A.
Figure 5D:
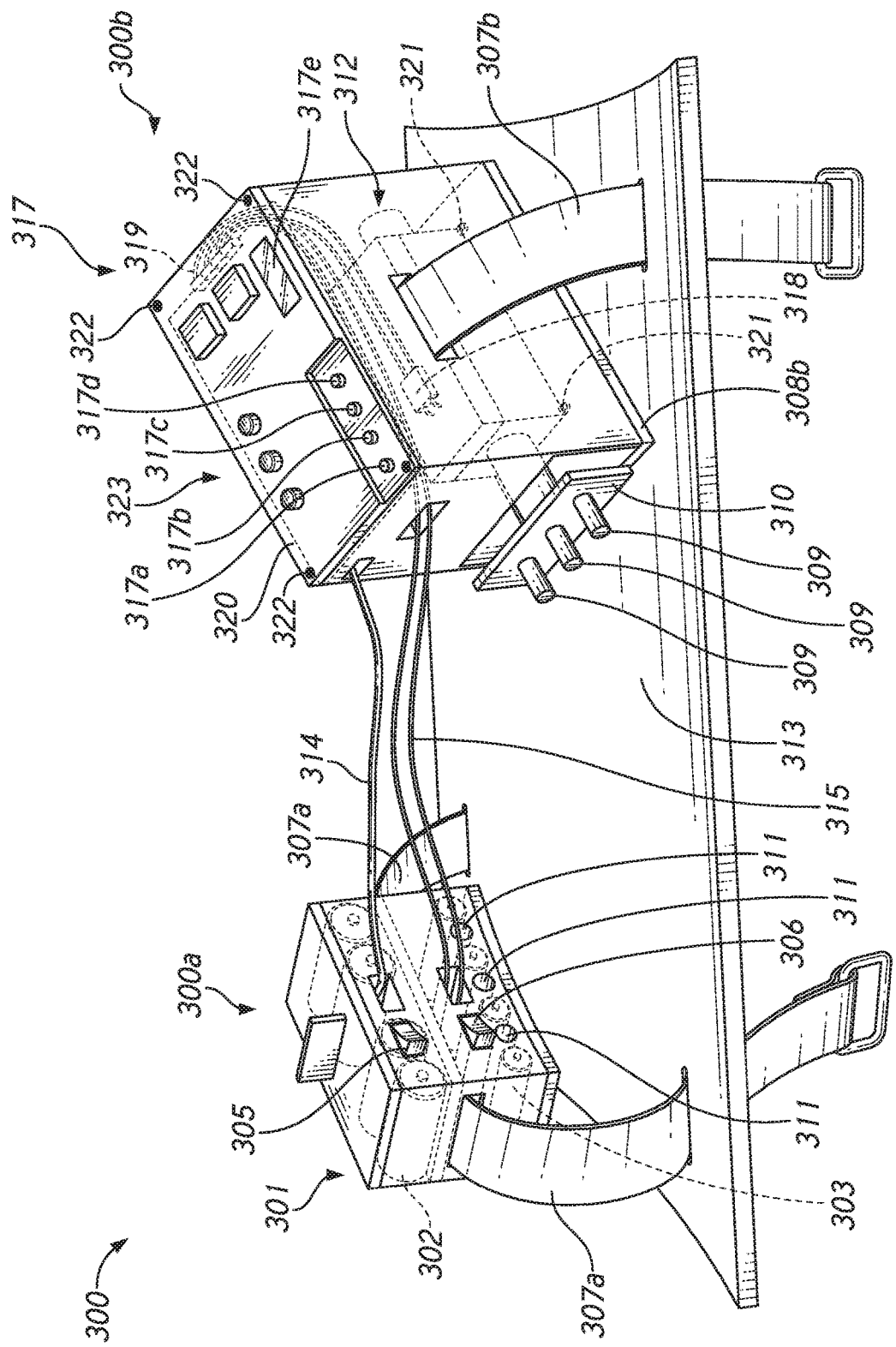
FIG. 5D is a partial cross-sectional perspective view of the wearable medical device shown in FIG. 5A.

As shown in FIG. 5A, the wearable device 300 can generally include a stretching mechanism, one or more straps 307a, 307b, a wrist contact portion 313 for receiving a user's forearm, and/or one or more contact portions 300a, 300b for contacting the user's arm opposite the wrist contact portion 313. Optionally, as shown in FIG. 5D, the wearable device 300 can include one or more battery packs 302, 303 to automate the stretching function. The stretching mechanism may include a rod adapter 310 including one or more rods 309, and/or an actuator 312 operatively connected to the rod adapter 310 and/or the one or more rods 309 (see FIGS. 5C-5D). The stretching mechanism of the wearable device 300 can be configured to apply opposing forces to the one or more contact portions 300a, 300b to stretch the user's tissue. The actuator 312 may drive the stretching mechanism. The one or more contact portions 300a, 300b can include a first contact portion 300a to contact the user's forearm at a first location and a second contact portion 300b to contact the user's forearm at a second location, different from the first location.

As previously described, the wearable device 300 can include a stretching mechanism configured to apply opposing forces to the first and second contact portions 300a, 300b to stretch the user's tissue. As shown in FIGS. 5C-5D, the stretching mechanism may include the actuator 312 that can apply a force to the rod adapter 310 and the one or more rods 309 such that opposing forces are applied the first and second contact portions 300a, 300b. For example, the second contact portion 300b can include the actuator 312 and the rod adapter 310 with the one or more rods 309 extending from the rod adapter 310. The first contact portion 300a can include one or more holes or apertures 311 configured to removably receive the one or more rods 309. In use, the actuator 312 can cause the one or more rods 309 to apply a force to the one or more apertures 311 of the first contact portion 300a such that opposing forces are applied to the first and second contact portions 300a, 300b. The stretching mechanism can be configured to intermittently or statically stretch the user's tissue. When stretch is not being applied to the underlying tissue, the first and second contacting portions 300a, 300b may be disconnected from each other. At least the one or more rods 309 may be separated from the apertures 311. In some configurations, the first and second contacting portions 300a, 300b may only be connected by the wrist contact portion 313 when a stretch is not being applied to the underlying tissue. In other configurations, the stretching mechanism may connect the first and second contact portions 300a, 300b when stretch is being applied and when stretch is not being applied. The stretching mechanism may control a distance between the first and second contact portions 300a, 300b to stretch the underlying tissue.

As shown in FIGS. 5A-5D, the wearable device 300 can include the wrist contact portion 313 for receiving a user's forearm. The wrist contact portion 313 may be constructed of a flexible material that enables the wrist contact portion 313 to be bent around the user's arm. For example, the wrist contact portion 313 may include a flexible fabric, elastic, plastic, rubber, or other material. The wrist contact portion 313 may define an arcuate shape and be adapted to support the forearm of the user. However, the wrist contact portion 313 may take on any configuration suitable for the patient to rest their forearm during treatment. For example, the wrist contact portion 313 may provide a planar surface for the user to rest their forearm. The wrist contact portion 313 may include one or more slots that can be configured to receive a portion of the one or more straps 307a, 307b, which is further described below. The one or more slots can be arranged near a periphery of the wrist contact portion 313.

The first and second contact portions 300a, 300b of the wearable device 300 can be adapted to transfer the vertical and/or non-vertical forces to the underlying tissue. For example, the first and second contact portions 300a, 300b may apply a compressive force to the user's forearm in a posterior-anterior direction. The two contact portions 300a, 300b may be adjusted relative to each other such that the contact portions 300a, 300b can be properly positioned. For example, a first contact portion 300a may be positioned over the user's carpal and/or metacarpal bones and a second contact portion 300b may be positioned over the user's radius and/or ulna bones. Each contact portion 300a, 300b may include a contact interface 308a, 308b and a strap of the one or more straps 307a, 307b. The contact interfaces 308a, 308b can be adapted for patient comfort when engaging the first and second contact portions 300a, 300b and/or to adhere or secure the respective contact portion 300a, 300b to the user's skin. For example, the contact interfaces 308a, 308b can include a rubber padding or an adhesive pad. The contact interfaces 308a, 308b may be replaceable. For example, a contact interface 308a, 308b including an adhesive pad may be replaced when the adhesive has worn off or is no longer sufficient for treatment. In some configurations, the wearable device 300 may come in a kit that includes a plurality of contact interfaces 308a, 308b that can be used to replace the contact interfaces 308a, 308b on the wearable device 300. The one or more straps 307a, 307b may be adapted to adjust the compressive force applied to the user's forearm by the first and second contact portions 300a, 300b. For example, a user can adjust the compressive force applied by the one or more contact portions 300a, 300b by tightening or loosening the one or more straps 307a, 307b.

The first contact portion 300a can comprise a battery case 304 with a battery case top 301. The battery case 304 can comprise the one or more batteries, which can be configured to power the actuator 312 and/or a push button relay 319. In some configurations, the one or more batteries can be located within the second contact portion 300b or external to the first and second contact portions 300a, 300b. The one or more batteries can include a first battery pack 302 and a second battery pack 303. The first battery pack 302 and the second battery pack 303 can include the same or different types of batteries. For example, the first battery pack 302 can be a 6V battery pack and the second battery pack 303 can be a 5V battery pack, or vice versa. Moreover, the first battery pack 302 and the second battery pack 303 can include the same type of batteries (e.g., both 6V or both 5V). Although two battery packs 302, 303 are shown in FIGS. 5B-5D, the wearable device 300 can include a single battery pack that powers the actuator 312 and/or the push button relay 319. The battery packs 302, 303 can be disposable and/or rechargeable. For example, the battery case top 301 can be configured to be removable such that the user can change the battery packs 302, 303 as needed. The battery case top 301 can include a finger grip to assist the user in removing the battery case top 301. The battery packs 302, 303 can be positioned on top of one another, as shown in FIGS. 5B-5D, or in different configurations (e.g., side by side). Each of the battery packs 302, 303 can include a respective battery holder 305, 306. The respective battery holders 305, 306 can each include a power switch. Each power switch can be configured to control whether the components of the medical device 300 is powered on or off. For example, the power switch associated with the first battery pack 302 may be turned on to allow the first battery pack 302 to power the actuator 312. The first contact portion 300a can include additional holes or apertures. For example, the first contact portion 300a can include an aperture for each battery pack 302, 303. Power cords 314, 315 corresponding to respective battery packs 302, 303 can pass through each aperture to the second contact portion 300b. In some configurations, the power cords 314, 315 are integrated within a single contact portion 300a, 300b such that the power cords 314, 315 do not travel from one contact portion 300a, 300b to the other contact portion 300a, 300b. For example, the one or more battery packs 302, 303 may be integrated with the second contact portion 300b.

The second contact portion 300b can comprise a push-button case 316 containing the actuator 312, the push-button relay 317, and one or more control buttons 323 (see FIG. 5D). The actuator 312 can be a linear actuator operatively connected to the rod adapter 310 and the one or more rods 309 of the rod adapter. The actuator 312 can be powered by the first or second battery pack 302, 303. For example, the actuator 312 can be powered by a 6V battery pack 302. The push-button case 316 can include an aperture to allow the power cord 315 of the actuator 312 to pass through to the associated battery pack 302. The actuator 312 can be secured to the interior of the push-button case 316. For example, the actuator 312 can be secured with a plurality of screws 321. Although, the actuator 312 is illustrated as being positioned at the bottom of the push-button case 316, the actuator 312 can be positioned elsewhere in the case 316. In some configurations, the actuator 312, the push-button relay 317, and one or more control buttons 323 can be located within the first contact portion 300a.

The push-button relay 317 can be integrated with or separate from a push-button top 320 of the push-button case 316. The actuator 312 can be configured to be controlled by the push-button relay 317 such that the push-button relay 317 can set the timing of one or more parameters of the actuator 312. For example, the push-button relay 317 can be programmable using one or more relay buttons 317a, 317b, 317c, 317d and a relay screen 317e. The one or more relay buttons 317a, 317b, 317c, 317d can comprise first, second, third, and fourth relay buttons 317a, 317b, 317c, 317d. Although four relay buttons 317a, 317b, 317c, 317d are shown in FIGS. 5A-5E, the wearable device 300 can have less than or more than four relay buttons 317a, 317b, 317c, 317d. The relay buttons 317a, 317b, 317c, 317d can be used with the relay screen 317e to program the timing of one or more parameters of the actuator 312. For example, the timing can include a forward period of time, a reverse period of time and one or more stop periods of time. The forward period of time can be the amount of time the push-button relay 317 drives the actuator 312 and the one or more rods 309 forward (e.g., into the first contact portion 300a such that the first contact portion 300a is pushed away from the second contact portion 300b) such that the device 300 applies opposing forces to the user's forearm. The forward period of time can be, for example, at least about 1 second and/or less than or equal to about 1 minute (e.g., 1 second, 5 seconds, 10 seconds, 15 seconds, 30 seconds). The reverse period of time can be the amount of time the push-button relay 317 drives the actuator 312 backward (e.g., away from the first contact portion 300a) such that the opposing forces being applied to the user's forearm are released. The reverse period of time can be, for example, at least about 1 second and/or less than or equal to about 1 minute (e.g., 1 second, 5 seconds, 10 seconds, 15 seconds, 30 seconds). The one or more stop periods of time can be the amount of time the actuator 312 maintains the opposing forces being applied to the user's forearm (e.g., after the forward period of time while the actuator 312 is engaged and in the forward position) and/or the amount of time the opposing forces are not being applied to the user's forearm (e.g., after the reverse period of time while the actuator 312 is disengaged and in the reverse position). The stop period of time can be, for example, at least about 1 second and/or less than or equal to about 1 minute (e.g., 1 second, 5 seconds, 10 seconds, 15 seconds, 30 seconds). In other configurations, the device 300 may be programmed to apply or reverse the opposing forces based on a parameter other than time, such as distance or force. Although the device 300 is described with an integrated user control interface, the device 300 may be controlled by an external device, for example as described in later embodiments.

To program the push-button relay 317, the user can use the one or more relay buttons 317a, 317b, 317c, 317d. For example, the user can use the first relay button 317a to select a functional mode of the push-button relay 317. The push-button relay 317 can have one or more functional modes. The user can use the first relay button 317a to cycle through the different functional modes, which can be displayed on the relay screen 317e. The user can select, for example, the "F-02" functional mode of the push-button relay 317. Once the "F-02" functional mode is selected (e.g., "F-02" is displayed on the relay screen 317e), the user can use the first, second, and third relay buttons 317a. 317b, 317c to program the different time parameters (e.g., the forward period of time, the reverse period of time, and the one or more stop periods of time). For example, the user can push the first relay button 317a to cycle through the different parameters. When the relay screen 317 displays the forward period of time, the user can use the second relay button 317b to increase the time and/or the third relay button 317c to decrease the time. Once the desired forward period of time is set, the user can use the first relay button 317a to set the reverse period of time and the one or more stop periods of time with the actuator in the forward position or reverse position using the second and third relay buttons 317b, 317c. With these parameters are set, the user can use the fourth relay button 317d to save the parameters such that the actuator 312 will operate according to these parameters for the duration of the treatment.

As shown in FIGS. 5A-5D, the push-button top 320 with the push-button relay 317 can be secured to the case 316, for example, with a plurality of screws 322. Alternatively, the push-button relay 317 can be positioned elsewhere on the push-button case 316 (e.g., a side of the case 316). A circuit board of the push-button relay 317 can be powered by the first battery pack 302 and the second battery pack 303 can be used to power the one or more relay buttons 317a, 317b, 317c, 317d and the actuator 312 concurrently. For example, the circuit board of the push-button relay 317 can be powered by a 6V battery pack 302. A power cord 314 can connect the push-button relay 317 with the first or second battery pack 303. In some configurations, the power cord 314 can include wires and/or a male barrel connected configured to attach to the push-button relay 317. The push-button relay 317 can also connect to the actuator 312. For example, a second power cord 319 of the actuator 312 can be connected to the push-button relay 317. In some configurations, the actuator 312 can be connected to a wire adapter 318 that is connected to the second power cord 319.

The one or more control buttons 323 can be integrated with or separate from the push-button top 320. The one or more control buttons 323 can be operatively connected to the push-button relay 317, which can be used to control the actuator 312. The one or more control buttons 323 can be configured to initiate and/or stop the treatment. For example, after the user programs the push-button relay 317, the user can push one of the control buttons 323 to initiate or stop the programmed treatment. Although three control buttons 323 are shown in FIGS. 5A-5D, the wearable device 300 can have less than or more than three control buttons 323.

Figure 5E:
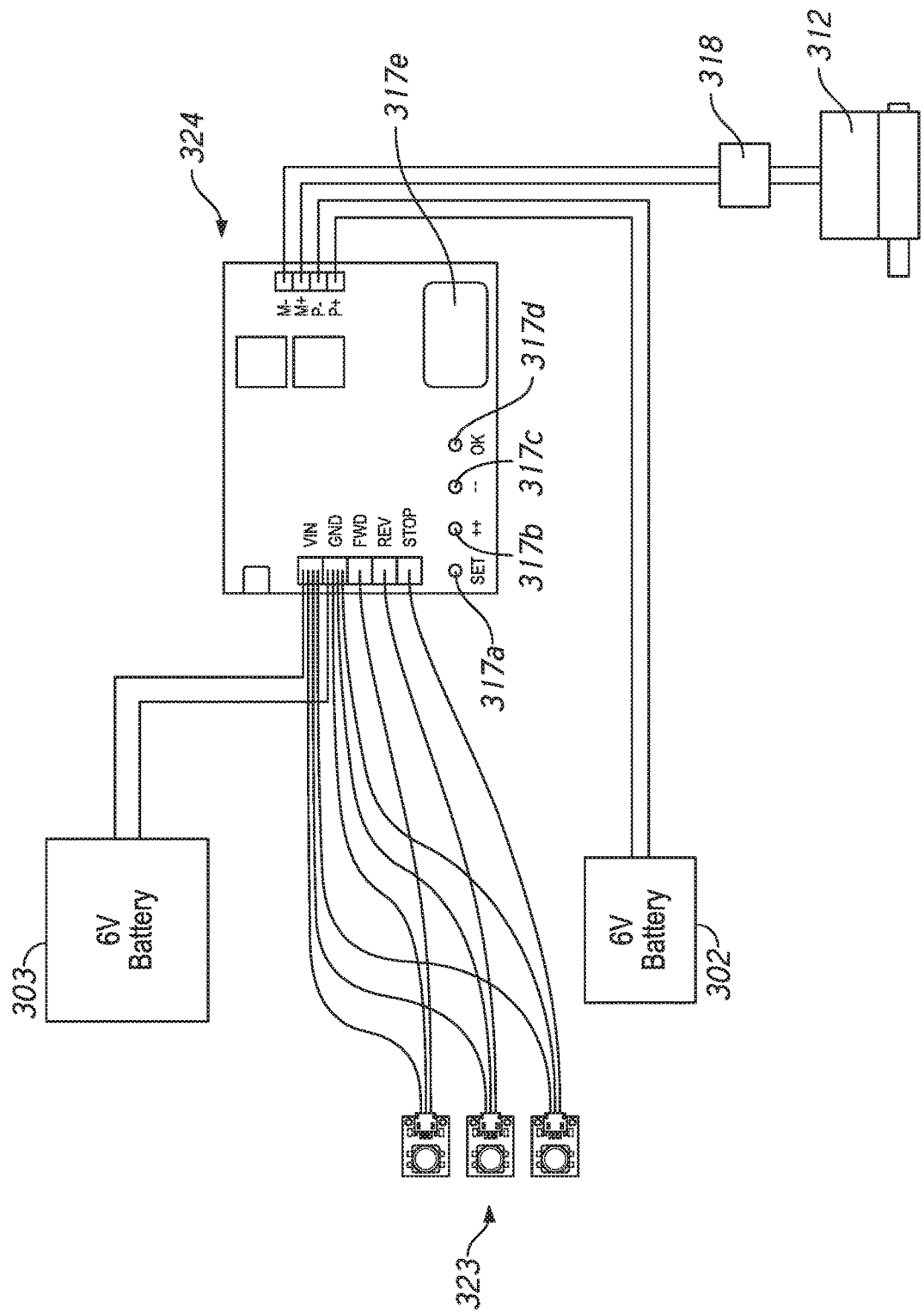
FIG. 5E is a schematic illustrating the wiring of the wearable medical device shown in FIG. 5A.

FIG. 5E illustrates a schematic of the wiring of the medical device 300. Control electronics 324 of the push-button relay 317 can be connected to the first and second battery packs 302, 303, the one or more control buttons 323, and the actuator 312. The actuator 312 can connect to the push-button relay 317 by the wire adapter 318.

In use, a user can place their forearm between the wrist contact portion 313, and the first and second contact portions 300a, 300b. The user can position one of the contact portions 300a, 300b on top of the user's carpal and/or metacarpal bones and the other contact portion 300a, 300b over the user's radius and/or ulna bones. The user can insert the one or more rods 309 into the one or more apertures 311. This may be done manually or automatically when the device is activated. The user may tighten the one or more straps 307a, 307b until the desired compressive force is applied. After the user secures the one or more straps 307a, 307b, the user can turn on the push-button relay 317 using the power switch of the second battery pack holder 305. The user can use the one or more relay buttons 317a, 317b, 317c, 317d to program the push-button relay 317. For example, the user can set the forward period of time, the one or more stop periods of time, and the reverse period of time. After the power-button relay 317 is programmed, the user can power on the actuator 312 using the power switch of the first battery pack holder 306. The actuator 312 can apply intermittent stretching to the user's forearm according to the parameters set on the push-button relay 317. For example, the device 300 can intermittently stretch the user's forearm for a set period of time (e.g., less than or equal to about 30 minutes, less than or equal to about 1 hour). In other configurations, the user can program the push-button relay 317 to apply static stretching to the user's forearm.

Figure 6A:
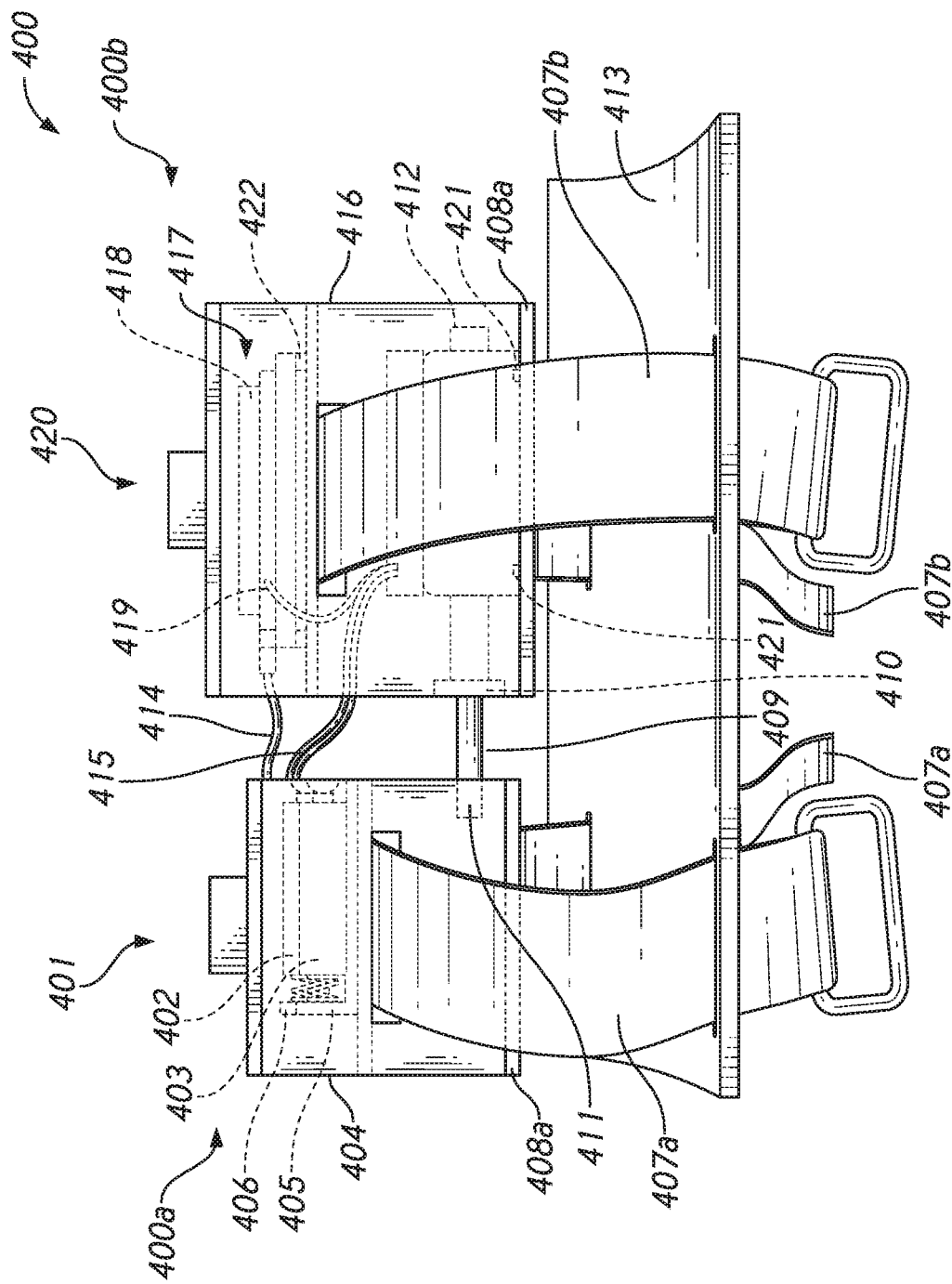
FIG. 6A is a partial cross-sectional side view of a wearable medical device.
Figure 6B:
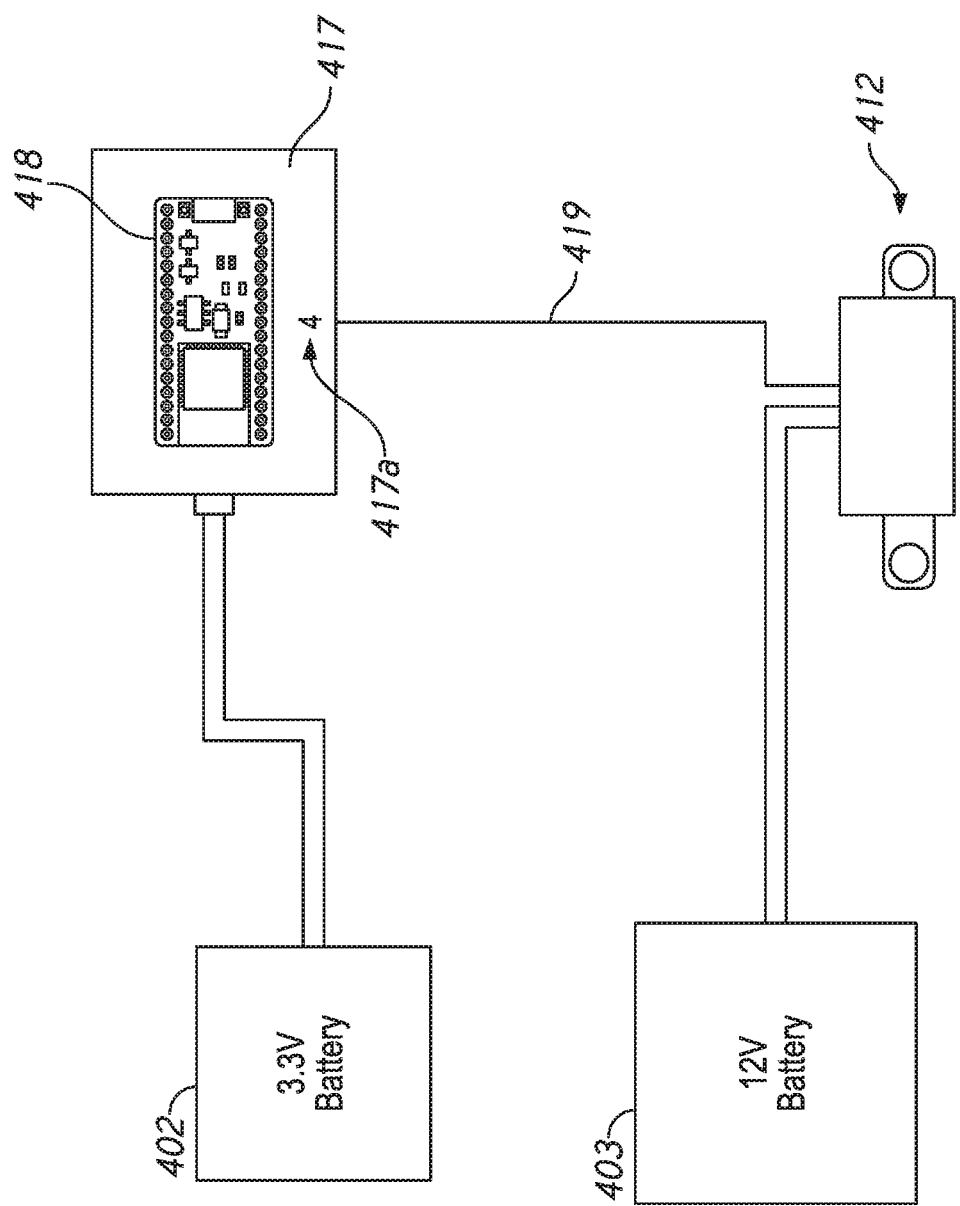
FIG. 6B is a schematic illustrating the wiring of the wearable medical device shown in FIG. 6A.

With reference to FIGS. 6A-6B, another configuration of a wearable medical device 400 is shown. The wearable device 400 resembles or is identical to the medical device 300 discussed above in many respects. Any component or step disclosed in any embodiment in this specification can be used in any other embodiment.

As shown in FIG. 6A, the wearable device 400 can generally include a stretching mechanism, one or more straps 407a, 407b, a wrist contact portion 413 for receiving a user's forearm, and/or one or more contact portions 400a, 400b for contacting the user's arm opposite the wrist contact portion 413. Optionally, the wearable device 400 can include one or more battery packs 402, 403 to automate the stretching function. The stretching mechanism may include a rod adapter 410 including one or more rods 409, and/or an actuator 412 operatively connected to the rod adapter 410 and/or the one or more rods 409. The stretching mechanism of the wearable device 400 can be configured to apply opposing forces to the one or more contact portions 400a, 400b to stretch the user's tissue. The actuator 412 may drive the stretching mechanism. The one or more contact portions 400a, 400b can include a first contact portion 400a to contact the user's forearm at a first location and a second contact portion 400b to contact the user's forearm at a second location, different from the first location.

As previously described, the wearable device 400 can include a stretching mechanism configured to apply opposing forces to the first and second contact portions 400a, 400b to stretch the user's tissue. The stretching mechanism may include the actuator 412 that can apply a force to the rod adapter 410 and the one or more rods 409 such that opposing forces are applied the first and second contact portions 400a, 400b. For example, the second contact portion 400b can include the actuator 412 and the rod adapter 410 with the one or more rods 409 extending from the rod adapter 410. The first contact portion 400a can include one or more holes or apertures 411 configured to removably receive the one or more rods 409. In use, the actuator 412 can cause the one or more rods 409 to apply a force to the one or more apertures 411 of the first contact portion 400a such that opposing forces are applied to the first and second contact portions 400a, 400b. The stretching mechanism can be configured to intermittently or statically stretch the user's tissue. When stretch is not being applied to the underlying tissue, the first and second contacting portions 400a, 400b may be disconnected from each other. At least the one or more rods 409 may be separated from the apertures 411. In some configurations, the first and second contacting portions 400a, 400b may only be connected by the wrist contact portion 413 when a stretch is not being applied to the underlying tissue. In other configurations, the stretching mechanism may connect the first and second contact portions 400a, 400b when stretch is being applied and when stretch is not being applied. The stretching mechanism may control a distance between the first and second contact portions 400a, 400b to stretch the underlying tissue.

As shown in FIG. 6A, the wearable device 400 can include the wrist contact portion 413 for receiving a user's forearm. The wrist contact portion 413 may be constructed of a flexible material that enables the wrist contact portion 413 to be bent around the user's arm. For example, the wrist contact portion 413 may include a flexible fabric, elastic, plastic, rubber, or other material. The wrist contact portion 413 may define an arcuate shape and be adapted to support the forearm of the user. However, the wrist contact portion 413 may take on any configuration suitable for the patient to rest their forearm during treatment. For example, the wrist contact portion 413 may provide a planar surface for the user to rest their forearm. The wrist contact portion 413 may include one or more slots that can be configured to receive a portion of the one or more straps 407a, 407b, which is further described below. The one or more slots can be arranged near a periphery of the wrist contact portion 413.

The first and second contact portions 400a, 400b of the wearable device 400 can be adapted to transfer the vertical and/or non-vertical forces to the underlying tissue. For example, the first and second contact portions 400a, 400b may apply a compressive force to the user's forearm in a posterior-anterior direction. The two contact portions 400a, 400b may be adjusted relative to each other such that the contact portions 400a, 400b can be properly positioned. For example, a first contact portion 400a may be positioned over the user's carpal and/or metacarpal bones and a second contact portion 400b may be positioned over the user's radius and/or ulna bones. Each contact portion 400a, 400b may include a contact interface 408a, 408b and a strap of the one or more straps 407a, 407b. The contact interfaces 408a, 408b can be adapted for patient comfort when engaging the first and second contact portions 400a, 400b and/or to adhere or secure the respective contact portion 400a, 400b to the user's skin. For example, the contact interfaces 408a, 408b can include a rubber padding or an adhesive pad. The contact interfaces 408a, 408b may be replaceable. For example, a contact interface 408a, 408b including an adhesive pad may be replaced when the adhesive has worn off or is no longer sufficient for treatment. The one or more straps 407a, 407b may be adapted to adjust the compressive force applied to the user's forearm by the first and second contact portions 400a, 400b. For example, a user can adjust the compressive force applied by the one or more contact portions 400a, 400b by tightening or loosening the one or more straps 407a, 407b.

The first contact portion 400a can comprise a battery case 404 with a battery case top 401. The battery case 404 can comprise the one or more batteries, which can be configured to power the actuator 412, and/or a communication module 418 and a terminal breakout block 417, as further described below. In some configurations, the one or more batteries can be located within the second contact portion 400b. The one or more batteries can include a first battery pack 402 and a second battery pack 403. The first battery pack 402 and the second battery pack 403 can include different types of batteries. For example, the first battery pack 402 can be a 3.3V battery pack and the second battery pack 403 can be a 12V battery pack, or vice versa. Moreover, the first battery pack 402 and the second battery pack 403 can include the same type of batteries (e.g., both 3.3V or both 12V). Although two battery packs 402, 403 are shown in FIG. 6A, the wearable device 400 can include a single battery pack that powers the actuator 412 and/or the communication module 418. The battery packs 402, 403 can be disposable and/or rechargeable. For example, the battery case top 401 can be configured to be removable such that the user can change the battery packs 402, 403 as needed. The top 401 may include a finger grip to assist the user in removing the top 401 from the battery case 404. The battery packs 402, 403 can be positioned side by side, as shown in FIG. 6A, or in different configurations (e.g., on top of one another). Each of the battery packs 402, 403 can include a respective battery holder 405, 406. The respective battery holders 405, 406 can each include a power switch. Each power switch can be configured to control whether the components of the medical device 400 is powered on or off. For example, the power switch associated with the first battery pack 402 may be turned on to allow the first battery pack 402 to power the actuator 412. The first contact portion 400a can include additional holes or apertures. For example, the first contact portion 400a can include an aperture for each battery pack 402, 403. Power cords 414, 415 corresponding to respective battery packs 402, 403 can pass through each aperture to the second contact portion 400b. In some configurations, the power cords 414, 415 are integrated within a single contact portion 400a, 400b such that the power cords 414, 415 do not travel from one contact portion 400a, 400b to the other contact portion 400a, 400b. For example, the one or more battery packs 402, 403 may be integrated with the second contact portion 400b.

As shown in FIG. 6A, the second contact portion 400b can comprise a case 416 containing the actuator 412 and a communication module 418. The actuator 412 can be a linear actuator operatively connected to the rod adapter 410 and the one or more rods 409 of the rod adapter. The actuator 412 can be powered by the first or second battery pack 402, 403. For example, the actuator 412 can be powered by a 12V battery pack 403. The case 416 can include an aperture to allow the power cord 415 of the actuator 412 to pass through to the associated battery pack 402. The actuator 412 can be secured to the interior of the case 416. For example, the actuator 412 can be secured with a plurality of screws 421. Although, the actuator 412 is illustrated as being positioned at the bottom of the case 416, the actuator 412 can be positioned elsewhere in the case 416.

The communication module 418 can be configured to transmit and/or receive data. For example, the communication module 418 can use any of a variety of wireless technologies, such as Wi-Fi (802.11x), Bluetooth, ZigBee, cellular telephony, infrared, RFID, satellite transmission, proprietary protocols, combinations of the same, and the like. In particular, the communication module 418 can use the Bluetooth wireless communications standard to communicate wirelessly with external devices (e.g., a user's smartphone). The communication module 418 can be positioned adjacent a top 420 of the case 416 or elsewhere in the case 416. The communication module 416 can be attached to a terminal breakout block 417 and the terminal breakout block 417 can be secured to the case 416 by a plurality of screws 422. The communication module 418 and the terminal breakout block 417 can be powered by the first or second battery pack 402, 403. For example, the communication module 418 and the terminal breakout block 417 can be powered by a 3.3V battery pack 402. A power cord 414 can connect the communication module 418 and the terminal breakout block 417 with the first or second battery pack 402, 403. The communication module 418 and the terminal breakout block 417 can also connect to the actuator 412. For example, a data cable 419 of the actuator 412 can be connected to the terminal breakout block 417. The data cable 419 can be configured transmit data between the communication module 418 and the actuator 412.

FIG. 6B illustrates a schematic of the wiring of the medical device 400. The actuator 412 can connect to a port 417a of the terminal breakout block 417 and the second battery pack 403. The terminal breakout block 417 can also connect to the first battery pack 402.

Figure 7:
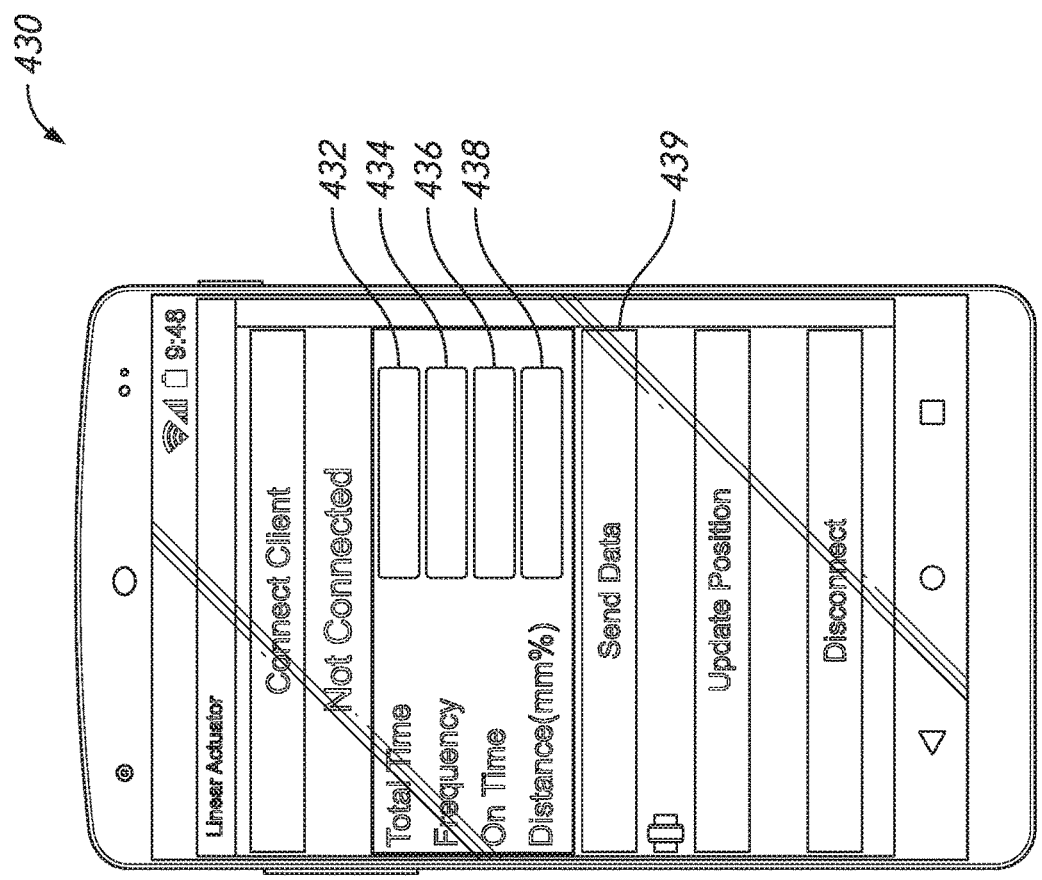
FIG. 7 illustrates an example user interface corresponding to a wearable device.

The medical device 400 can be configured to communicate with a user computing device 430 (e.g., a smartphone, a laptop computer, a desktop computer, a smart watch). Other configurations of the medical device 300, 500 can also be configured to communicate with the user computing device 430. The user computing device 430 can be configured to run an application associated with the medical device 400. FIG. 7 illustrates an example user computing device 430 running the associated application. A user can input certain user parameters 432, 434, 436, 438 into the application. For example, the user can input a total time 432 for the treatment, for example at least about 10 minutes and/or less than or equal to about 1 hour (e.g., 0.5 hours, 1 hour), a frequency 434 of activations of the actuator 412, an on time 436 for the actuator 412, and/or a distance 438 the actuator 412 extends when activated. The actuator 412 can be activated when the terminal breakout block 417 drives the actuator 412 forward (e.g., into the first contact portion 400a such that the first contact portion 400a is pushed away from the second contact portion 400b) to the set distance 438 (e.g., less than or equal to about 5 millimeters, less than or equal to about 10 millimeters, less than or equal to about 15 millimeters) such that the device 400 applies opposing forces to the user's forearm. The on time 436 can be the amount of time the actuator 412 is held at the set distance 438, for example at least about 5 seconds and/or less than or equal to about 1 minute (e.g., 5 seconds, 10 seconds, 15 seconds, 30 seconds). The frequency 434 of activations of the actuator 412 can be the number of times the actuator 412 is activated within a certain period of time (e.g., less than or equal to about 100 activations per hour, less than or equal to about 200 activations per hour, less than or equal to about 300 activations per hour, less than or equal to about 400 activations per hour). In other configurations, the device 400 may be programmed to apply or reverse the opposing forces based on a parameter other than time and distance, such as force. Although the device 400 is described as being controlled by an external device (e.g., the user computing device 430), the device 400 may be controlled by an integrated control interface, for example as described in earlier embodiments.

In use, a user can place their forearm between the wrist contact portion 413, and the first and second contact portions 400a, 400b. The user can position one of the contact portions 400a, 400b on top of the user's carpal and/or metacarpal bones and the other contact portion 400a, 400b over the user's radius and/or ulna bones. The user can insert the one or more rods 409 into the one or more apertures 411 and tighten the one or more straps 407a, 407b until the desired compressive force is applied. After the user secures the one or more straps 407a, 407b, the user can turn on the first and second battery packs 402, 403 using the respective power switches. The user can input user parameters 432, 434, 436, 438 into the associated application on the user computing device 430. The user can press the "Send Data" button 429 (shown in FIG. 7) to start the treatment. The actuator 412 can apply intermittent stretching to the user's forearm according to the user parameters 432, 434, 436, 438 set on the associated application on the user computing device 430. For example, the device 400 can intermittently stretch the user's forearm for the total time 432 (e.g., less than or equal to about 0.5 hours, less than or equal to about 1 hour). In other configurations, the user can use the medical device 400 to apply static stretching to the user's forearm.

With reference to FIGS. 8A-8D, another configuration of a wearable medical device 500 is shown. The wearable device 500 resembles or is identical to the medical device 300 discussed above in many respects. Any component or step disclosed in any embodiment in this specification can be used in any other embodiment.

Figure 8B:
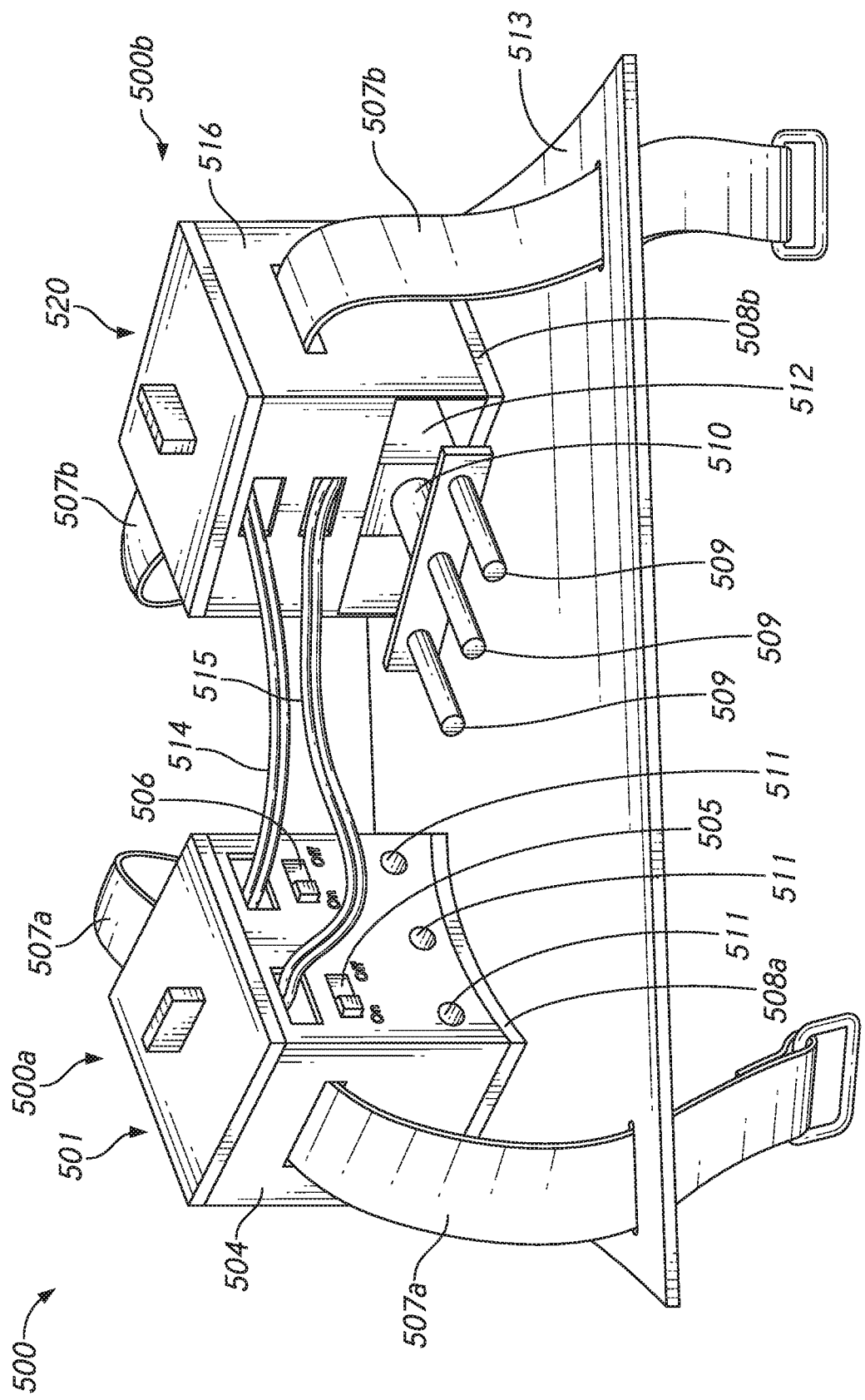
FIG. 8B is a perspective view of the wearable medical device shown in FIG. 8A.
Figure 8C:
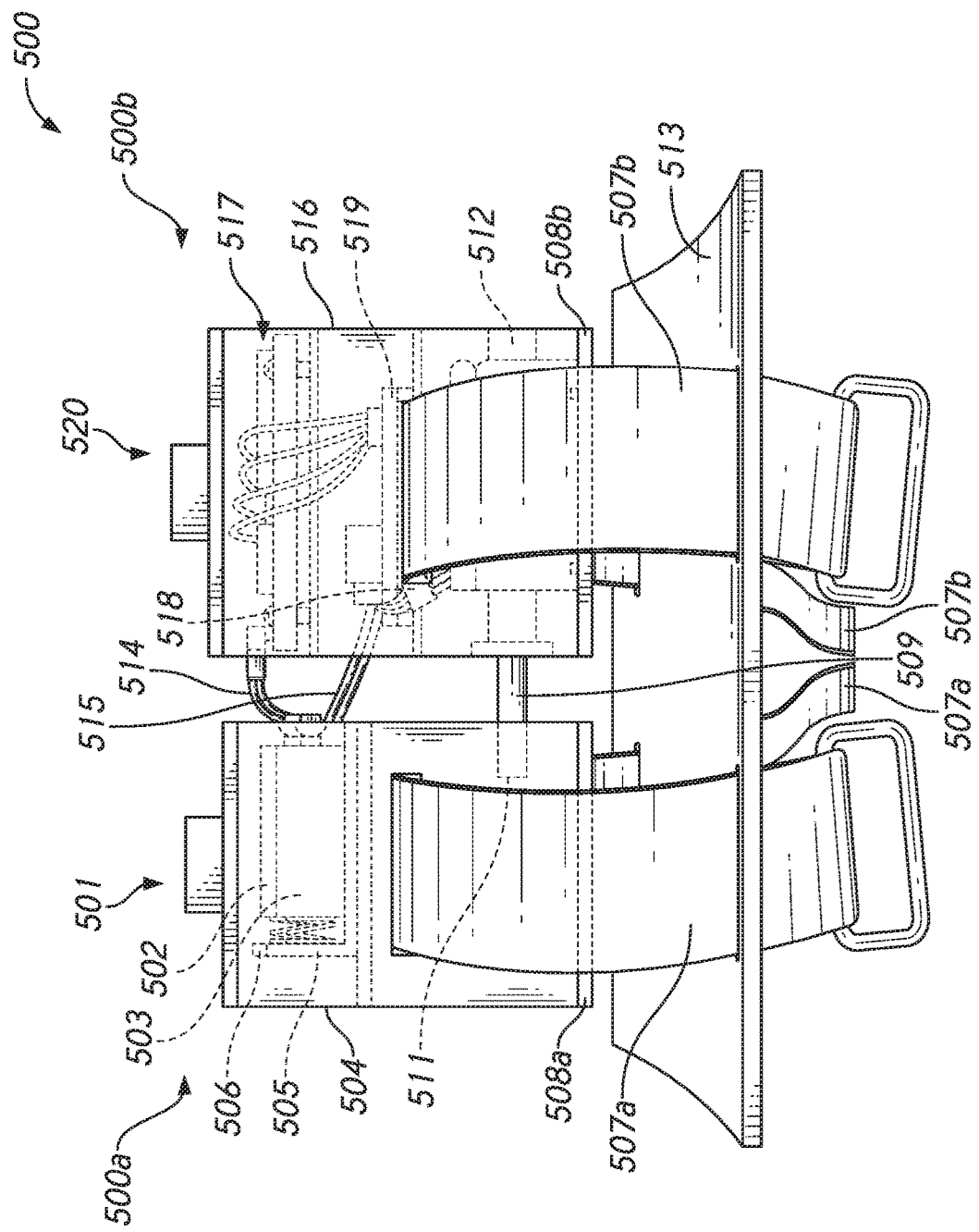
FIG. 8C is a partial cross-sectional perspective view of the wearable medical device shown in FIG. 8A.

As shown in FIG. 8A the wearable device 500 can generally include a stretching mechanism, one or more straps 507a, 507b, a wrist contact portion 513 for receiving a user's forearm, and/or one or more contact portions 500a, 500b for contacting the user's arm opposite the wrist contact portion 513. Optionally, as shown in FIG. 8C, the wearable device 500 can include one or more battery packs 502, 503 to automate the stretching function. The stretching mechanism may include a rod adapter 510 including one or more rods 509, and/or an actuator 512 operatively connected to the rod adapter 510 and/or the one or more rods 509 (see FIG. 8B). The stretching mechanism of the wearable device 500 can be configured to apply opposing forces to the one or more contact portions 500a, 500b to stretch the user's tissue. The actuator 512 may drive the stretching mechanism. The one or more contact portions 500a, 500b can include a first contact portion 500a to contact the user's forearm at a first location and a second contact portion 500b to contact the user's forearm at a second location, different from the first location.

As previously described, the wearable device 500 can include a stretching mechanism configured to apply opposing forces to the first and second contact portions 500a, 500b to stretch the user's tissue. The stretching mechanism may include the actuator 512 that can apply a force to the rod adapter 510 and the one or more rods 509 such that opposing forces are applied the first and second contact portions 500a, 500b. For example, the second contact portion 500b can include the actuator 512 and the rod adapter 510 with the one or more rods 509 extending from the rod adapter 510. The first contact portion 500a can include one or more holes or apertures 511 configured to removably receive the one or more rods 509. In use, the actuator 512 can cause the one or more rods 509 to apply a force to the one or more apertures 511 of the first contact portion 500a such that opposing forces are applied to the first and second contact portions 500a, 500b. The stretching mechanism can be configured to intermittently or statically stretch the user's tissue. When stretch is not being applied to the underlying tissue, the first and second contacting portions 500a, 500b may be disconnected from each other. At least the one or more rods 509 may be separated from the apertures 511. In some configurations, the first and second contacting portions 500a, 500b may only be connected by the wrist contact portion 513 when a stretch is not being applied to the underlying tissue. In other configurations, the stretching mechanism may connect the first and second contact portions 500a, 500b when stretch is being applied and when stretch is not being applied. The stretching mechanism may control a distance between the first and second contact portions 500a, 500b to stretch the underlying tissue.

As shown in FIG. 8A, the wearable device 500 can include the wrist contact portion 513 for receiving a user's forearm. The wrist contact portion 513 may be constructed of a flexible material that enables the wrist contact portion 513 to be bent around the user's arm. For example, the wrist contact portion 513 may include a flexible fabric, elastic, plastic, rubber, or other material. The wrist contact portion 513 may define an arcuate shape and be adapted to support the forearm of the user. However, the wrist contact portion 513 may take on any configuration suitable for the patient to rest their forearm during treatment. For example, the wrist contact portion 513 may provide a planar surface for the user to rest their forearm. The wrist contact portion 513 may include one or more slots that can be configured to receive a portion of the one or more straps 507a, 507b, which is further described below. The one or more slots can be arranged near a periphery of the wrist contact portion 513.

The first and second contact portions 500a, 500b of the wearable device 500 can be adapted to transfer the vertical and/or non-vertical forces to the underlying tissue. For example, the first and second contact portions 500a, 500b may apply a compressive force to the user's forearm in a posterior-anterior direction. The two contact portions 500a, 500b may be adjusted relative to each other such that the contact portions 500a, 500b can be properly positioned. For example, a first contact portion 500a may be positioned over the user's carpal and/or metacarpal bones and a second contact portion 500b may be positioned over the user's radius and/or ulna bones. Each contact portion 500a, 500b may include a contact interface 508a, 508b and a strap of the one or more straps 507a, 507b. The contact interfaces 508a, 508b can be adapted for patient comfort when engaging the first and second contact portions 500a, 500b and/or to adhere or secure the respective contact portion 500a, 500b to the user's skin. For example, the contact interfaces 508a, 508b can include a rubber padding or an adhesive pad. The one or more straps 507a, 507b may be adapted to adjust the compressive force applied to the user's forearm by the first and second contact portions 500a, 500b. For example, a user can adjust the compressive force applied by the one or more contact portions 500a, 500b by tightening or loosening the one or more straps 507a, 507b.

The first contact portion 500a can comprise a battery case 504 with a battery case top 501. The battery case 504 can comprise the one or more batteries, which can be configured to power the actuator 512 and/or, a control circuit 517 and a relay module 519, as further described below. In some configurations, the one or more batteries can be located within the second contact portion 500b. The one or more batteries can include a first battery pack 502 and a second battery pack 503. The first battery pack 502 and the second battery pack 503 can include the same type of batteries. For example, the first and second battery packs 502, 503 can include 12V batteries. Moreover, the first battery pack 502 and the second battery pack 503 can include different types of batteries. Although two battery packs 502, 503 are shown in FIG. 8C, the wearable device 300 can include a single battery pack that powers the actuator 312 and/or the push button relay 319. The battery packs 502, 503 can be disposable and/or rechargeable. For example, the battery case top 501 can be configured to be removable such that the user can change the battery packs 502, 503 as needed. The top 501 can include a finger grip to assist the user in removing the top 501. The battery packs 502, 503 can be positioned side by side, as shown in FIGS. 8B-8C, or in different configurations (e.g., on top of one another). Each of the battery packs 502, 503 can include a respective battery holder 505, 506. The respective battery holders 505, 506 can each include a power switch. Each power switch can be configured to control whether the components of the medical device 500 is powered on or off. For example, the power switch associated with the first battery pack 502 may be turned on to allow the first battery pack 502 to power the control circuit 517. The first contact portion 500a can include additional holes or apertures. For example, the first contact portion 500a can include an aperture for each battery pack 502, 503. Power cords 514, 515 corresponding to respective battery packs 502, 503 can pass through each aperture to the second contact portion 500b. In some configurations, the power cords 514, 515 are integrated within a single contact portion 500a, 500b such that the power cords 514, 515 do not travel from one contact portion 500a, 500b to the other contact portion 500a, 500b. For example, the one or more battery packs 502, 503 may be integrated with the second contact portion 500a, 500b.

The second contact portion 500b can comprise a case 516 containing the actuator 512, the control circuit 517, and the relay module 519 (see FIG. 8C). The actuator 512 can be a linear actuator operatively connected to the rod adapter 510 and the one or more rods 509 of the rod adapter 510. The actuator 512 can be configured to be controlled by the control circuit 517. The actuator 512 can have an original position and a forward position. When the actuator 512 is in the forward position, the one or more rods 509 can apply a force against the first contact portion 500a such that the actuator 512 applies opposing forces to the first and second contact portion 500a, 500b. When the actuator 512 is in the original position, the actuator 512 does not apply opposing forces to the first and second contact portions 500a, 500b. The actuator 512 can be powered by the first or second battery pack 502, 503. For example, the actuator 512 can be powered by a 12V battery pack 503. The case 516 can include one or more apertures to allow the power cord 515 of the actuator 512 to pass through to the associated battery pack 503. The actuator 512 can be secured to the interior of the case 516. Although, the actuator 512 is illustrated as being positioned at the bottom of the case 516, the actuator 512 can be positioned elsewhere in the case 516.

The control circuit 517 can be configured to run an algorithm to control different components of the medical device 500. For example, the control circuit 517 can control the relay module 519 and the actuator 512. In particular, the algorithm can include certain aspects that can be adjustable by the user. For example, the user can adjust the algorithm on a user computing device (e.g., a smartphone, a laptop computer, a desktop computer) to set certain user parameters for the treatment. The user parameters include: an amount of time the actuator 512 will move forward (e.g., into the first contact portion 500a such that the first contact portion 500a is pushed away from the second contact portion 500b) from the original position to the forward position, an amount of time the actuator 512 will remain in the forward position, and/or an amount of time the actuator 512 will move backward (e.g., away from the first contact portion 500b) from the forward positon to the original positon. The control circuit 517 can be positioned adjacent the top 520 of the case 516. Alternatively, the control circuit 517 can be positioned elsewhere on the case 516. The control circuit 517 can be powered by the first or second battery pack 502, 503. For example, the control circuit 517 can be powered by a 12V battery pack 502. A power cord 514 can connect the control circuit 517 with the first or second battery pack 502, 503. The power cord 514 of the control circuit 517 can pass through one of the one or more apertures of the case 516 to the associated battery pack 502. The control circuit 517 can also connect to the relay module 519. In other configurations, the device 500 may be programmed to apply or reverse the opposing forces based on a parameter other than time, such as distance or force. Although the device 500 is described as being controlled by an external device (e.g., the user computing device), the device 500 may be controlled by an integrated control interface, for example as described in earlier embodiments.

The relay module 519 may be, for example, a two channel relay module. The relay module 519 can be positioned adjacent the control circuit 517. For example, the relay module 519 may be positioned between the control circuit 517 and the actuator 512. The relay module 519 can be powered by the first or second battery pack 502, 503. For example, the relay module 519 can be powered by a 12V battery pack 503. The power cord 515 can power both the actuator 512 and the relay module 519. Alternatively, the actuator 512 and the relay module 519 may be powered by separate power cords. The relay module 519 can be connected to the control circuit 517 and/or the actuator 512. A wire adapter 518 can be used to connect the relay module 519 to the actuator 512.

Figure 8D:
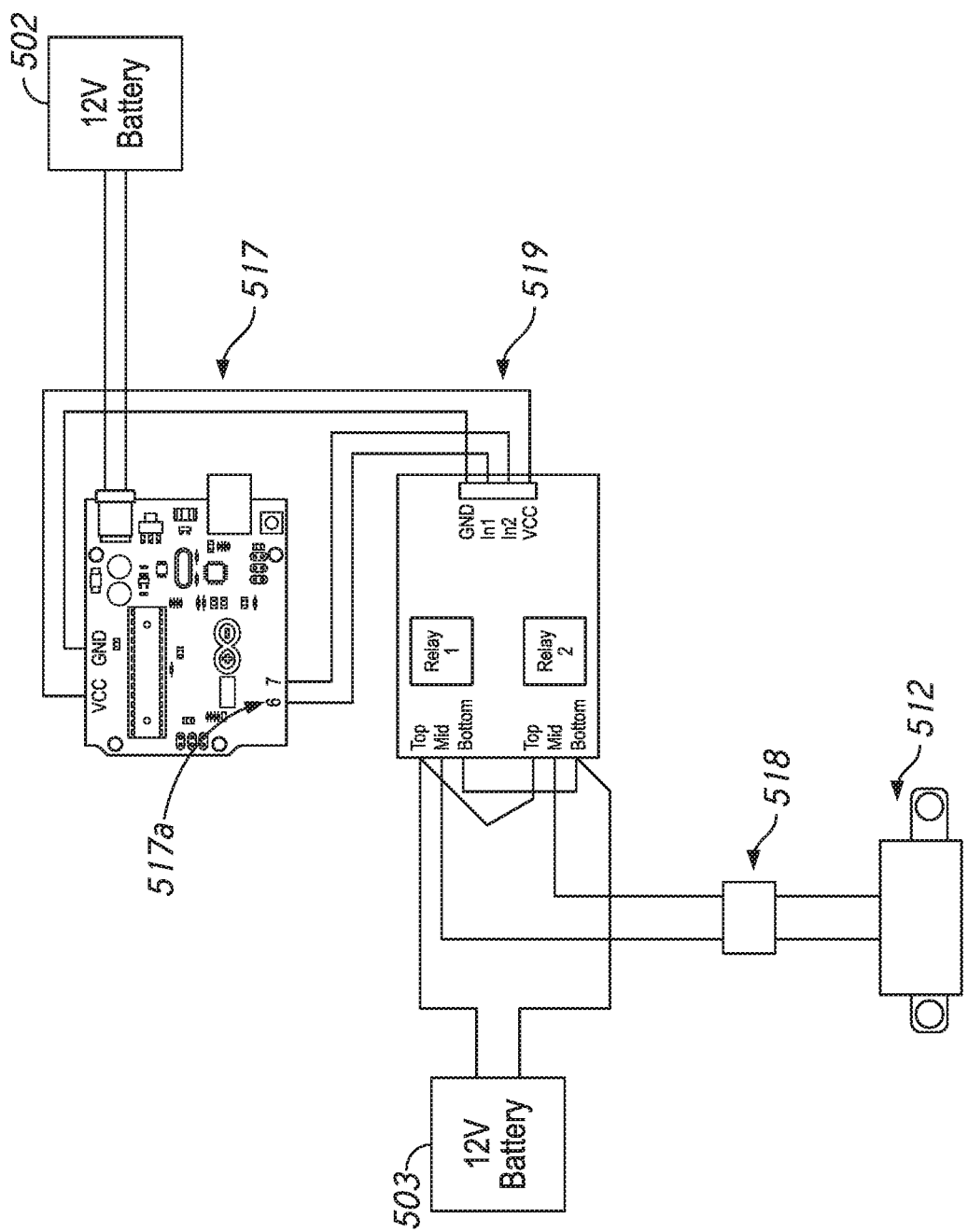
FIG. 8D is a schematic illustrating the wiring of the wearable medical device shown in FIG. 8A.

FIG. 8D illustrates a schematic of the wiring of the medical device 500. The control circuit 517 can be connected to the relay module 519 via one or more output ports 517a of the control circuit 517 and the first battery pack 502. The relay module 519 may be connected to the control circuit 517, the second battery pack 503, and the actuator 512 via adapter 518.

In use, a user can adjust the timing programming code to set an amount of time the actuator 512 will move forward from an original position to a forward position (e.g., less than or equal to about 1 second, less than or equal to about 5 seconds, less than or equal to about 10 seconds, less than or equal to about 15 seconds), an amount of time the actuator 512 will remain in the forward position (e.g., less than or equal to about 5 seconds, less than or equal to about 15 seconds, less than or equal to about 30 seconds), an amount of time the actuator 512 will move backward from the forward positon to the original positon (e.g., less than or equal to about 1 second, less than or equal to about 5 seconds, less than or equal to about 10 seconds, less than or equal to about 15 seconds). The user can send the adjusted algorithm to the control circuit 517. The user can place their forearm between the wrist contact portion 513, and the first and second contact portions 500a, 500b. The user can position one of the contact portions 500a, 500b on top of the user's carpal and/or metacarpal bones and the other contact portion 500a, 500b over the user's radius and/or ulna bones. The user can insert the one or more rods 509 into the one or more apertures 511 and tighten the one or more straps 507a, 507b until the desired compressive force is applied. After the user secures the one or more straps 507a, 507b, the user can turn on both battery pack 502, 503. The actuator 512 can apply intermittent stretching to the user's forearm according to the user parameters. For example, the device 500 can intermittently stretch the user's forearm for a set period of time, for example at least about 10 minutes and/or less than or equal to about 1 hour (e.g., 30 minutes, 1 hour). In other configurations, the user can program the device 500 to apply static stretching to the user's forearm.

Terminology

Although the devices and methods have been described herein in connection with preventing and/or treating carpal tunnel or DeQuervain's syndromes in a user's forearm, the devices and methods described herein can be used to release myofascial restrictions in any portion of the user's body. For example, in some embodiments, the wrist contacting portion of the medical devices described herein can be adapted to receive the user's upper arm or a portion of the user's leg.

As used herein, the relative terms "anterior," "posterior," "proximal," and "distal" shall be defined from the perspective of the user's hand. Thus, anterior refers to the direction of the user's palm and posterior refers to the opposite side of the user's hand. Also, distal refers to the direction of the user's fingertips and proximal refers to the direction of the user's elbow.

Note that the terms "first" and "second" contact portion can be used interchangeably and may refer to either contact portion. Although certain embodiments have been described herein with certain components located in a first contact portion and certain components located in a second contact portion, the components may be located in either contact portion or differently combined.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Phrases preceded by a term such as "generally" include the recited phrase and should be interpreted based on the circumstances (e.g., as much as reasonably possible under the circumstances). For example, "generally vertical" includes "vertical."

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

What is claimed is:

1. A wearable device for preventing and/or treating carpal tunnel syndrome or DeQuervain's syndrome, the wearable device comprising:
    a support portion for receiving a user's forearm;
    a stretching mechanism comprising a first contact portion and a second contact portion, the stretching mechanism being configured to apply opposing forces to the first contact portion and the second contact portion to stretch the user's tissue,
        wherein the first contact portion is configured to contact the user's forearm and apply a compressive force to the user's forearm at a first location,
        wherein the second contact portion is configured to contact the user's forearm on a same side of the user's forearm as the first contact portion, the second contact portion configured to apply a compressive force to the user's forearm at a second location different than the first location, and
        wherein the first contact portion is configured to removably connect to the second contact portion; and
    one or more straps configured to adjust the compressive force being applied to the user's forearm by the first and second contact portions.

2. The wearable device of claim 1, wherein the stretching mechanism is configured to apply the opposing forces in a direction generally perpendicular to the compressive forces applied by the first and second contact portions.

3. The wearable device of claim 1, wherein the one or more straps are configured to adjust a distance between the first and second contact portions relative to the support portion.

4. The wearable device of claim 3, wherein the support portion comprises one or more slots, wherein the one or more straps are configured to pass through the one or more slots.

5. The wearable device of claim 1, wherein the one or more straps comprise a hook and loop fastener configured to secure a position of the first and second contact portions relative to the support portion.

6. The wearable device of claim 1, wherein the stretching mechanism comprises an actuator configured to adjust the opposing forces applied to the first and second contact portions.

7. The wearable device of claim 1, wherein the second contact portion of the stretching mechanism comprises one or more rods extending from the second contact portion, and the first contact portion of the stretching mechanism comprises one or more apertures configured to removably receive the one or more rods.

8. The wearable device of claim 7, wherein the one or more rods of the second contact portion are configured to transfer a force to the one or more apertures of the first contact portion such that the opposing forces are applied to the first and second contact portions.

9. The wearable device of claim 1, wherein the second contact portion comprises one or more user actuators, the one or more user actuators are configured to adjust one or more parameters of the opposing forces applied to the first and second contact portions.

10. The wearable device of claim 1, wherein the second contact portion comprises one or more user actuators, the one or more user actuators are configured to initiate and/or stop the application of the opposing forces to the first and second contact portions.

11. The wearable device of claim 1, wherein the first contact portion of the stretching mechanism comprises at least one compression spring positioned over at least one compression spring guide and the second contact portion of the stretching mechanism comprises at least one spring guide receptor configured to removably receive the at least one compression spring guide.

12. The wearable device of claim 10, wherein the at least one compression spring is configured to apply opposing forces to the first and second contact portions in use.

13. The wearable device of claim 1, wherein the first contact portion further comprises a first connector and the second contact portion further comprises a second connector, wherein the second connector comprises a buckle and the first connector comprises a buckle receptor configured to removably receive the buckle.

14. A method for preventing and/or treating carpal tunnel syndrome or DeQuervain's syndrome, the method comprising:

positioning the user's forearm on a wrist contact portion of a wearable device;
contacting a first contact portion of the wearable device with a posterior side of the user's forearm over carpal and/or metacarpal bones at a first location;
contacting a second contact portion of the wearable device with the posterior side of the user's forearm over a radius and/or an ulna bone at a second location different from the first location;
aligning one or more rods of the second contact portion of the wearable device with one or more apertures of the first contact portion of the wearable device;
applying a compressive force to the user's forearm using one or more straps connected to the first and second contact portions and the wrist contact portion; and
applying opposing forces to the first contact portion and the second contact portion using a stretching mechanism to stretch the user's tissue.

15. The method of claim 14, wherein applying the opposing forces comprises applying the opposing forces in a direction generally perpendicular to the compressive force applied by the first and second contact portions.

16. The method of claim 14, wherein the stretching mechanism comprises an actuator configured to apply a force to the one or more rods of the second contact portion, wherein the one or more rods transfers the force from the actuator to the one or more apertures such that the opposing forces are applied to the first and second contact portions.

17. The method of claim 14, further comprising, prior to applying opposing forces to the first and second contact portions, setting one or more user parameters to apply opposing forces to the first and second contact portions according to the one or more user parameters.

18. The method of claim 17, wherein the one or more user parameters comprises: a forward period of time, a first stop period of time, a second stop period of time and/or a reverse period of time.

19. The method of claim 18, wherein applying the opposing forces to the first and second contact portions comprises:
automatically initiating the application of the opposing forces for the forward period of time;
automatically applying the opposing forces to the first and second contact portions for the first stop period of time;
automatically releasing the opposing forces applied to the first and second contact portions for the reverse period of time; and
automatically allowing the user's tissue to rest for the second stop period of time.

20. The method of claim 19, further comprising, after automatically allowing the user's tissue to rest:
automatically reinitiating the application of the opposing forces for the forward period of time;
automatically reapplying the opposing forces for the first stop period of time;
automatically releasing the opposing forces for the reverse period of time; and
automatically allowing the user's tissue to rest for the second stop period of time until treatment is complete.

* * * * *